US007674832B2

(12) United States Patent
Higuchi

(10) Patent No.: US 7,674,832 B2
(45) Date of Patent: Mar. 9, 2010

(54) COMPOSITIONS FOR PROMOTING WOUND HEALING AND TREATING PSORIASIS

(76) Inventor: Maira de Lourdes Higuchi, Rua Capote Valente, 361 - ap. 142, Sao-Paulo (BR) 05409-001

( * ) Notice: Subject to any disclaimer, the term of this patent is extended or adjusted under 35 U.S.C. 154(b) by 67 days.

(21) Appl. No.: 12/033,204

(22) Filed: Feb. 19, 2008

(65) Prior Publication Data

US 2009/0068167 A1 Mar. 12, 2009

Related U.S. Application Data

(63) Continuation-in-part of application No. 10/952,003, filed on Sep. 28, 2004, now Pat. No. 7,335,638, which is a continuation-in-part of application No. PCT/BR03/00049, filed on Mar. 28, 2003.

(60) Provisional application No. 60/890,980, filed on Feb. 21, 2007.

(51) Int. Cl.
*A01N 25/00* (2006.01)

(52) U.S. Cl. ...................................................... 514/783

(58) Field of Classification Search .................. 514/783
See application file for complete search history.

(56) References Cited

U.S. PATENT DOCUMENTS

| | | | |
|---|---|---|---|
| 5,596,091 | A | 1/1997 | Switzer |
| 6,281,199 | B1 | 8/2001 | Gupta |
| 7,108,851 | B2 | 9/2006 | Higuchi et al. |
| 7,335,638 | B2 | 2/2008 | Higuchi |
| 2003/0124109 | A1 | 7/2003 | Higuchi et al. |
| 2005/0142116 | A1 | 6/2005 | Higuchi |
| 2009/0148432 | A1 | 6/2009 | Higuchi |

FOREIGN PATENT DOCUMENTS

| | | |
|---|---|---|
| WO | WO/02/02050 | 1/2002 |
| WO | WO/03/082324 | 10/2003 |
| WO | WO/2006/034560 | 4/2006 |

OTHER PUBLICATIONS

Mar. 21, 2006 Notice of Allowance in U.S. Appl. No. 10/086,913.
Nov. 9, 2005 Response to Final Office Action in U.S. Appl. No. 10/086,913.
Oct. 24, 2005 Notice of Allowance in U.S. Appl. No. 10/086,913.
Jul. 29, 2005 Response to Non-Final Office Action in U.S. Appl. No. 10/086,913.
Jan. 27, 2005 Non-Final Office Action in U.S. Appl. No. 10/086,913.
Oct. 1, 2007 Notice of Allowance in U.S. Appl. No. 10/952,003.
Sep. 7, 2007 Request for Continued Examination in U.S. Appl. No. 10/952,003.
Jul. 30, 2007 Notice of Allowance in U.S. Appl. No. 10/952,003.
Apr. 23, 2007 Response to Non-Final Office Action in U.S. Appl. No. 10/952,003.
Jan. 23, 2007 Non-Final Office Action in U.S. Appl. No. 10/952,003.
Agusti et al., 1997, "The trans-sialidase of Trypanosome cruzi is anchored by two different lipids," Glycobiology, vol. 7, No. 6: p. 731-735.
Aiello, et al., 2002, "A possible role for complement in the pathogenesis of chronic chagasic cardiomyopathy," Journal of Pathology, vol. 197: p. 224-229.
Akira et al., "Toll-like receptors: critical proteins linking innate and acquired immunity," Nature Immunol. 2:675-680(2001).
Amaya, et al., 2004, "Structural Insights into the catalytic mechanism of Trypanosoma cruzi trans-sialidase," Structure, vol. 12: p. 775 784.
Amend et al., "Energetics of overall metabolic reactions of thermophilic and hyperthermophilic archaea and bacteria," F.E.M.S. Microbiol. Rev. 25: 175-243 (2001).
Baseman, et al., 1982, "Sialic acid residues mediate Mycoplasma pneumoniae attachment to human and sheep erythrocytes," Infect. Immun., vol. 38, No. 1: p. 389-391.
Berbec, et al., 1999, "Total serum sialic acid concentration as a supporting marker of malignancy in ovarian neoplasia," Eur. J. Gynaecol On Col., vol. 20, No. 5-6: p. 389-392.
Blanchard, et al., 1994, "AIDS-associated mycoplasmas," Annu. Rev. Microbiol., vol. 48: p. 687-712.
Bredt, et al., 1982, "Adherence of mycoplasmas: phenomena and possible role in the pathogenesis of disease," Infection, vol. 10, No. 3: p. 199-201.
Briones, et al., 1993, "Trypanosoma cruzi trans-sialidase homologue," Accession No. AAC98544, GI:624626, 736 aa.
Buscaglia, et al., 1998, "The repetitive domain of Trypanosome cruzi trans-sialidase enhances the immune response against the catalytic domain," J. Infect. Dis., vol. 177, No. 2: p. 431-436.
Buscaglia, et al., 1999, "Tandem amino acid repeats from Trypanosoma cruzi shed antigens increase the half-life of proteins in blood," Blood, vol. 93: p. 2025-2032.
Buschiazzo, et al., 1996, "Medium scale production and purification to homogeneity of a recombinant trans-sialidase from Trypanosoma cruzi," Cell Mol. Biol., vol. 42: p. 703-710.
Buschiazzo, et al., 2002, "The Crystal Structure and Mode of Action of Trans-sialidase, a key enzyme in Trypanosoma cruzi pathogenesis," Molecular Cell, vol. 10: p. 757-758.
Campetella, et al., 1994, "A recombinant Trypanosoma cruzi trans-sialidase lacking the amino acid repeats retains the enzymatic activity," Mol. Biochem. Parasitol., vol. 64: p. 337-340.
Chandler, et al., 1982, "Mycoplasma pneumoniae attachment: competitive inhibition by mycoplasmal binding component and by sialic acid-containing glycoconjugates," Infect. Immun., vol. 38, No. 2: p. 598-603.
Chen et al., "Apoptosis of hepatoma cells SMMC-7721 induced by Ginkgo biloba seed polysaccharide," World J. Gastroenterol. 8: 832-6 (2002).

(Continued)

*Primary Examiner*—Maryam Monshipouri
(74) *Attorney, Agent, or Firm*—Baker Botts LLP

(57) ABSTRACT

The present invention relates to compositions and methods for promoting healing of cutaneous, mucosal and/or mucocutaneous lesions associated with the presence of a mycoplasma and one or more non-mycoplasma microorganisms. The compositions and methods of the invention also relate to the reduction of joint pain, column pain, and/or skeletal muscle pain.

7 Claims, 7 Drawing Sheets

OTHER PUBLICATIONS

Chen et al., 1986, "Carditis associated with Mycoplasma pneumoniae infection," Am. J. Dis. Child., vol. 140: p. 471-472.
Clyde et al., "Tropism for Mycoplasma gallisepticum for arterial walls," Proc. Natl. Acad. Sci. U.S.A. 70: 1545-1549 (1973).
Cole, 1997 "Mycoplasma interactions with the immune system: implications for disease pathology," http://www.compkarori.com/arthritis/pil6002.htm.
Cole, 1999, "Mycoplasma-induced arthritis in animals: relevance to understanding the etiologies of the human rheumatic diseases," Rev. Rhum. Engl. Ed. 66, 1Suppl: p. 45S-49S.
Collier and Clyde, "Relationships between M. pneumoniae and human respiratory epithelium," Infect. Immun. 3:694-701 (1971).
Cremona, et al., 1995, "A single tyrosine differentiates active and inactive Trypanosome cruzi trans-sialidase," Gene, vol. 160: p. 123-128.
Cremona, et al., 1996, "Effect of primary structure modifications in Trypanosoma cruzi neuramindase trans-sialidase activities," Cell. Mol. Biol., vol. 42: p. 697-702.
Dallo, et al., 2000, "Intracellular DNA replication and long term survival of pathogenic mycoplasmas" Microbial Pathogenesis vol. 29: p. 301-309.
Damy et al., "Coinfection of laboratory rats with Mycoplasma pulmonis and Chlamydia pneumoniae," Contemp. Top.Am.Assoc. Lab.An.Sci. 42: 52-56 (2003).
Danesch, et al., 1997, "Chronic infections and coronary artery disease: is there a link?" Lancet, vol. 350: p. 430-436.
Fagundes RQ. Study of co-participation of natural infection by Chlamydophila pneumoniae and Mycoplasma pneumoniae in experimental atherogenesis in rabbits. Doctoral thesis presented at the Heart Institute of Clinical Hospitial, in the Cardiology Sciences Post Graduation Program of São Paulo University School of Medicine, Mar. 17, 2006. (The Summary is in the English language).
Farraji, et al., 1997, "Mycoplasma-associated pericarditis," Mayo Clin. Proc., vol. 72: p. 33-36.
Fearon et al., "Cancer cachexia," Int. J. Cardiol 85: 73-81 (2002).
Feng Shaw-Huey, et al., 1999, "Mycoplasma infections prevent apoptosis and induce malignant transformation of interleukin-3-dependent 32D hematopoietic cells," Mol. Cel. Biol., vol. 19, No. 12: p. 7995-8002.
Florin THJ et al., "Shared and unique environmental factors determine the ecology of methanogens in humans and rats," Am. J. Gastroenterol. 95: 2872-2879 (2000).
Fu et al., 1998, "Middle cerebral artery occlusion after recent Mycoplasma pneumoniae infection," J. Neurol. Sci., vol. 157: p. 113-115.
Gabridge and Taylor-Robinson, "Interaction of Mycoplasma pneumoniae with human lung fibroblasts: role of receptor sites," Infect. Immun. 25:455-459 (1979).
Giles et al., "Androgenetic alopecia and prostate cancer: findings from an Australian case-control study," Cancer Epidemiol. Biomarkers Prev 11: 549-553 (2002).
Glasgow and Hill, "Interactions of Mycoplasma gallisepticum with sialyl glycoproteins," Infect. Immun. 30:353-361 (1980).
Gurfinkel, et al., 1997, "IgG antibodies to chlamydial and mycoplasma infection plus C-reactive protein related to poor outcome in unstable angina," Arch. Inst. Cardiol. Mex., vol. 67: p. 462-468.
Hansen, et al., 1981, "Characterization of hemadsorption-negative mutants of Mycoplasma pneumoniae," Infect. Immun., vol. 32: p. 127-136.
Higuchi et al., "Mycoplasma pneumoniae and Chlamydia pneumoniae in calcified nodules of aortic stenotic valves," Rev Inst Med trop S.Paulo 44:209-212 (2002).
Higuchi et al., 2000, "Detection of Mycoplasma pneumoniae and Chlamydia pneumoniae in ruptured atherosclerotic plaques," Braz. J. Med. Biol. Res. 33:1023-1026.
Higuchi et al., 2006, "Co-infection ratios versus inflammation, growth factors and progression of early atheromas," APMIS, 114(5):338-44.
Higuchi, et al., 1987, "The role of active myocarditis in the development of heart failure in chronic chagas disease: a study based on endomycardial biopsies," Clin. Cardiol., vol. 10: p. 665-670.
Higuchi, et al., 1997, "Association of an increase in CD8+T cells with the presence of Trypanosoma cruzi antigens in chronic human chagasic mycoarditis," Am. J. Trop. Med. Hyg., vol. 56, No. 5: p. 485-489.
Higuchi, et al., 2000, "Great amount of C. pneumoniae in ruptured plaque vessel segments at autopsy. A comparative study of stable plaques," Ara. Bras. Cardiol., vol. 74: p. 149-151.
Higuchi, et al., 2003, "Pathophysiology of the heart in chagas' disease: current status and new developments" European Society of Cardiology, pp. 96-107.
Higuchi, et al., 2003, "Coinfection with Mycoplasma pneumoniae and Chlamydia pneumoniae in ruptured plaques associated with acute myocardia infarction," Arq. Bras. Cardiol., vol. 81, No. 1: p. 12-22.
Higuchi, et al., 2004, "Trypanosoma cruzi trans-sialidase as a new therapeutic tool in the treatment of chronic inflammatory disease: possible action against mycoplasma and chlamydia," Medical Hypotheses, vol. 63: p. 616-623.
Horne, et al., 2000, "IgA sero-positivity to Mycoplasma pneumoniae predicts the diagnosis of coronary artery disease," J. Am. Coll. Cardiol., vol. 35: p. 321 (abstract).
Howland et al., The surprising archaea. Discovering another domain of life. Oxford University Press. (New York, 2000). (Table of Contents Only).
Huber J et al., "A new phylum of Archaea represented by a nanosized hyperthermophilic symbiont," Nature 417: 63-67 (2002).
Izumikawa et al., 1986, "Mycoplasma Pneumoniae Attachment to Glutaraldehyde-Treated Human WiDr Cell Cultures," Proc. of the Soc. for Exp. Biol. and Med, vol. 181, No. 4, pp. 507-511.
Kahane et al., 1981, "Attachement of mycoplasmas to epithelium of the host respiratory tract," Isr. J. Med. Sci., vol. 17: p. 589-592.
Kahane, 1983, "Purification of attachment moiety: a review," Yale J. Biol. Med., vol. 53: p. 665-669.
Kaji, et al., 2005, "A Side effect of neuraminidase inhibitor in a patient with liver cirrhosis," J. Infect. Chemother, vol. 11: p. 41-43.
Kloetzel, et al., 1984, "Trypanosoma cruzi interaction with macrophages: differences between tissue culture and bloodstream forms." Rev. Inst. Med. Trop. Sao Paulo., vol. 26: p. 179-185.
Krause et al., 1982, "Identification of Mycoplasma pneumoniae proteins associated with hemadsorption and virulence," Infect. Immun., vol. 35: p. 809-817.
Laroy, et al., 2000, "Cloning of Trypanosoma cruzi trans-Sialidase and Expression in Pichia pastoris," Protein Expr. Purif., vol. 20: p. 389-393.
Libby, et al., 1986, "A Neuraminidase from Tyranosoma cruzi removes sialic acid from the surface of mammalian myocardial and endothelial cells," J. Clin. Invest., vol. 77: p. 127-135.
Maida, et al., 1983, "Immunological reactions against Mycoplasma pneumoniae in multiple sclerosis: preliminary findings," J. Neurol., vol. 229, No. 2: p. 103-111.
Maniloff et al. Eds., Mycoplasmas, Molecular Biology and Pathogenesis. American Society for Microbiology. (Washington, 1992). (Table of Contents).
Maraha, et al., 2000, "Is Mycoplasma pneumoniae associated with vascular disease," J. Clin. Microbiol., vol. 38: p. 935-936.
Milner, "A historical perspective on garlic and cancer," J. Nutr. 131: 1027S-1031S. (2001).
Monto, et al., 1999, "Efficacy and Safety of the Neuraminidase Inhibitor Zanamivir in the treatment of Influenza A and B Virus Infections," Journal of Infectious Diseases, vol. 180: p. 254-261.
Muhlradt, "Immunomodulation by mycoplasmas: artifacts, facts and active molecules," in Molecular Biology and Pathogenicity of Mycoplasmas. Eds Razin S & Herrman R, 2002, academic Kluwer/ Plenum Publishers, New York, p. 445-472.
Neyrolles et al., 1998, "Identification of two glycosylated components of Mycoplasma penetrans: a surface-exposed capsular polysaccharide and a glycolipid fraction," Microbiology, vol. 144: p. 1247-1255.
Nicolson, et al., 1999, "Mycoplasmal infections in chronic illnesses," Medical Sentinel, vol. 4: p. 172-175, 191.

Ong et al., "Detection and widespread distribution of Chlamydia pneumoniae in the vascular system and its possible implications," J. Clin. Pathol. 49:102-106 (1996).
Palomino, et al., 2000, "Systematic mapping of hearts from chronic chagasic patients: the association between the occurrence of histopathological lesions and Trypanosoma cruzi antigens Annals of Tropical Medicine and Parasitology," vol. 94, No. 6: p. 571-579.
Parodi, et al., 1992, "Identification of the gene(s) coding for the trans-sialidase of Trypanosome cruzi" EMBO J., vol. 11: p. 1705-1710.
Pereira et al., "Lectin receptors as markers for Trypanosoma cruzi. Development stages and a study of the interaction of wheat germ agglutinin with sialic acid residues on epimastigotes cells," J. Exp. Med., 152:1375-1392 (1980).
Pereira et al., "The Trypanosoma cruzi neuraminidase contains sequences similiar to bacterial neuraminidases, YWTD repeats of the low density lipoprotein receptor, and Type III modules of fibronection," J. Ex. Med. 174:179-191 (1991).
Pereira, 1983, "A developmentally regulated neuraminidase activity in Trypanosoma cruzi," Science, vol. 219: p. 1444-1446.
Perez, et al., 1997, "Leukocytoclastic vasculitis and polyarthritis associated with Mycoplasma pneumoniae infection," Clin. Infect. Dis., vol. 25: p. 154-155.
Pollevick, et al., 1991, "The complete sequence of a shed acute-phase antigen of Trpanosoma cruzi," Mol. Biochem. Parasitol., vol. 47: p. 247-250.
Razin et al. Eds., Molecular biology and pathogenicity of mycoplasmas, Kluwer Academic/Plenum Publishers (New York, 2002) (Table of Contents Only).
Razin, et al., 1998, "Molecular biology and pathogenicity of mycoplasmas," Microbiol. Mol. Biol. Rev., vol. 62, No. 4: p. 1094-1156.
Ribeirao, et al., 1997, "Temperature difference for trans-glycosylation and hydrolysis reaction reveal an acceptor binding site in the catalytic mechanism of Trypanosoma cruzi trans-sialidase," Glycobiology, vol. 7: p. 1237-1246.
Richards et al., "Prolactin is an antagonist of TGF-beta activity and promotes proliferation of murine B cell hybridomas," Cel. Immunol. 184: 85-91 (1998).
Roberts, et al., 1989, "Sialic Acid-dependent Adhesion of Mycoplasma pneumoniae to Purified Glycoproteins," Journal of Biological Chemistry, vol. 264: p. 9289-9293.
Rodrigues-Amaya, "Latin American food sources of carotenoids," Arch. Latinoam. Nutr. 49: 74S-84S (1999).
Ros-Bullon, et al., 1999, "Serum sialic acid in malignant melanoma patients: na ROC curve analysis," Anticancer Res., vol. 19, No. 4C: p. 3619-3622.
Sachse, et al., 1996, "Mechanisms and factors involved in Mycoplasma bovis adhesion to cells," Int. J. of Med. Microbiology, vol. 284: p. 80-92.
Sambiase, et al., 2000, "CMV and transplant-related coronary atherosclerosis: an immunohistochemical, in situ hybridization and polymerase chain reaction in situ study," Modern Pathology, vol. 13: p. 173-179.
Schenkman, et al., 1991, "Attachment of Trypanosoma cruzi trypomastigotes to receptors at restricted cell surface domains," Exp. Parasitol., vol. 72: p. 76-86.
Schenkman, et al., 1992, "Trypanosoma cruzi trans-sialidase and neuraminidase activities can be mediated by the same enzymes," J. Exp Med, vol. 175, No. 2: p. 567-575.
Schenkman, et al., 1994, "A proteolytic fragment of Trypanosoma cruzi trans-sialidase lacking the carboxy-terminal domain is active, monomeric, and generates antibodies that inhibit enzymatic activity," J. Biol. Chem., vol. 269: p. 7970-7975.
Schenkman, et al, 1994, "Structural and functional properties of Trypano-some trans-sialidase," Annu. Rev. Microbiol., vol. 48: p. 499-523.
Scudder, et al., 1993, "Enzymatic characterization of beta-D-galactoside alpha 2, 3-trans-sialidase from Trypanosome cruzi," J. Biol. Chem., vol. 268, No. 13, p. 9886-9891.
Sengupta A et al., "Administration of garlic and tomato can protect from carcinogen induced clastogenicity," Nutrit. Res. 22: 859-866 (2002).
Silva and Nussenzweig, 1953, "Sobre uma cepa deTrypanosoma cruzi altamente virulenta para o camundongo branco." Folia Clin Biol, vol. 20: p. 191-203.
Simecka, et al., 1992, "Mycoplasmas Diseases of Animals," in Maniloff et al. Eds., Mycoplasmas. Molecular Biology and Pathogenesis, American Society of Microbiology: p. 391-415.
Smith, et al., 1996, Trypanosoma cruzi trans-silaidase, Accession No. BAA09333, GI:840706, 964 aa.
Smith, et al., 1996, Trypanosoma cruzi trans-silaidase, Accession No. BAA09334, GI:840708, 1060 aa.
Sobeslavsky, et al., 1968, Adsorption of Mycoplasma pneumonia to neuraminic acid receptors of various cells and possible role in virulence by Journal of Bacteriology, p. 695-705.
Taylor-Robinson and Thomas, 1998, "Chlamydia pneumoniae in arteries: the facts, their interpretation, and future studies," J. Clin. Pathol., vol. 51: p. 793-797.
Taylor-Robinson, et al., 1981, "Mycoplasmal adherence with particular reference to the pathogenicity of Mycoplasma pulmonis," Isr. J. Med. Sci., vol. 17: p. 599-603.
Timms, "Vertex baldness link to prostate cancer," Lancet Oncology 3:584 (2002).
Treanor, et al., 2000, "Efficacy and Safety of the Oral Neuraminidase Inhibitor Oseltamivir in Treating Acute Influenza," JAMA, vol. 283.
Tsai, et al., 1995, "Mycoplasmas and onogenesis: persistent infection and multistage malignant transformation," Proc. Natl. Acad. Sci. U.S.A., vol. 92, No. 22: p. 10197-10201.
Uchide et al., "Effect of antioxidants on apoptosis induced by influenza virus infection: inhibition of viral gene replication and transcription with pyrrolidine dithiocarbamate," Antiviral Res. 56: 207-217 (2002).
Uemura et al., Trypanosoma cruzi trans-sialidase-neuraminidase, Accession No. S28409, GI:323067, 200 aa, Jan. 2000.
Uemura, et al., 1992, "Only some memeber of a gene family in Trypanosome cruzi encode proteins that express both trans-sialidase and neuraminidase," EMBO J., vol. 11: p. 3837-3844.
Uemura, et al., 1995, "Trypanosoma cruzi TCTS-121 gene for trans-sialidase," Accession No. D50685, GI:840707, 3183 bp.
Uemura, et al., 1995, "Trypanosoma cruzi TCTS-154 gene for trans-sialidase," Accession No. D50684, GI:840705, 2895 bp.
Umezawa, et al., 1996, "Immunobolt assay using excreted/secreted antigens of Trypanosoma cruzi in serodiagnosis of congenital, acute and chronic Chagas' disease," J. Clin. Microbiol., vol. 34: p. 2143-2147.
Umezawa, et al., 2001, "Enzyme-linked immunosorbent assay with Trypanosoma cruzi excreted-secreted antigens (TESA-ELISA) for serodiagnosis of acute and chronic Chagas' disease," Diag. Microbiol. Infect. Dis., vol. 39: p. 169-176.
Val'kovich, 1980, "Viral and mycoplasma-induced glomerulopathies in children," Arkh. Pathol. 42(3):10-15. (Article is in the Russian language. English abstract is provided).
Vanderkerckhove, et al., 1992, "Substrate specificity of the Trypanosoma cruzi trans-sialidase," Glycobiology, vol. 2, No. 6: p. 541-548.
Walsmith et al., "Cachexia in rheumatoid arthritis," Int. J. Cardiol. 85: 89-99 (2002).
Wang et al., "The role of endotoxin, TNF-alpha, and Il-6 in inducing the state of growth hormone insensitivity," World J. Gastroenterol. 8: 531-536 (2002).
Watts, et al., 2003, "Trypanosoma cruzi trans-sialidase operates through a covalent sialyl-enzyme intermediate: Tryosine is the catalytic nucleophile," J. Am. Chem. Soc., vol. 125: p. 7532-7533.
Winther et al., "Effects of Ginkgo biloba extract on cognitive function and blood pressure in elderly subjects," Curr. Therap. Res. 59: 881-888 (1998).
Woese, et al., 1977, "Phylogenetic structure of the prokaryotic domain: the primary kingdoms," Proc. Natl. Acad. Sci. U.S.A., vol. 74: p. 5088-5090.
Woody et al., "Prolactin exerts hematopoietic growth-promoting effects in vivo and partially counteracts myelosuppression by azidothymidine," Exp. Hematol. 27: 811-816 (1999).
Zipes, et al., 2005, Braunwald's Heart Disease, Elsevier Saunders, Philadelphia (Table of Contents only).

A. C.

B. D.

Figure 3.
SEQ ID NO:3

```
ATGGGCAGCA GCCATCATCA TCATCATCAC AGCAGCGGCC TGGTGCCGCG CGGCAGCCAT 60
Atggcacccg gatcgagccg agttgagctg tttaagcggc aaagctcgaa ggtgccattt 120
gaaaagggcg gcaaagtcac cgagcgggtt gtccactcgt tccgcctccc cgcccttgtt 180
aatgtggacg gggtgatggt tgccatcgcg gacgctcgct acgaaacatc caatgacaac 240
tccctcattg atacggtggc gaagtacagc gtggacgatg gggagacgtg ggagacccaa 300
attgccatca agaacagtcg tgcatcgtct gtttctcgtg tggtggatcc cacagtgatt 360
gtgaagggca acaagcttta cgtcctggtt ggaagctaca acagttcgag gagctactgg 420
acgtcgcatg gtgatgcgag agactgggat attctgcttg ccgttggtga ggtcacgaag 480
tccactgcgg gcggcaagat aactgcgagt atcaaatggg ggagccccgt gtcactgaag 540
gaatttttcc cggcggaaat ggaaggaatg cacacaaatc aatttcttgg cggtgcaggt 600
gttgccattg tggcgtccaa cgggaatctt gtgtaccctg tgcaggttac gaacaaaaag 660
aagcaagttt tttccaagat cttctactcg gaagacgagg gcaagacgtg gaagtttggg 720
gagggtagga gtgattttgg ctgctctgaa cctgtggccc ttgagtggga ggggaagctc 780
atcataaaca ctcgagttga ctatcgccgc cgtctggtgt acgagtccag tgacatgggg 840
aattcgtggg tggaggctgt cggcacgctc tcacgtgtgt ggggcccctc accaaaatcg 900
aaccagcccg gcagtcagag cagcttcact gccgtgacca tcgagggaat gcgtgttatg 960
ctcttcacac acccgctgaa ttttaaggga aggtggctgc gcgaccgact gaacctctgg 1020
ctgacggata accagcgcat ttataacgtt gggcaagtat ccattggtga tgaaaattcc 1080
gcctacagct ccgtcctgta caaggatgat aagctgtact gtttgcatga gatcaacagt 1140
aacgaggtgt acagccttgt tttgcgcgc ctggttggcg agctacggat cattaaatca 1200
gtgctgcagt cctggaagaa ttgggacagc cacctgtcca gcatttgcac ccctgctgat 1260
ccagccgctt cgtcgtcaga gcgtggttgt ggtcccgctg tcaccacggt tggtcttgtt 1320
ggcttttgt cgcacagtgc caccaaaacc gaatgggagg atgcgtaccg ctgcgtcaac 1380
gcaagcacgg caaatgcgga gagggttccg aacggtttga agtttgcggg ggttggcgga 1440
ggggcgcttt ggccggtgag ccagcagggg cagaatcaac ggtatcactt tgcaaaccac 1500
gcgttcacgc tggtggcgtc ggtgacgatt cacgaggttc cgagcgtcgc gagtcctttg 1560
ctgggtgcga gcctggactc ttctggtggc aaaaaactcc tggggctctc gtacgacgag 1620
aagcaccagt ggcagccaat atacggatca acgccggtga cgccgaccgg atcgtgggag 1680
atgggtaaga ggtaccacgt ggttcttacg atggcgaata aaattggttc ggtgtacatt 1740
gatggagaac ctctggaggg ttcagggcag accgttgtgc cagacgggag gacgcctgac 1800
atctcccact tctacgttgg cgggtatgga aggagtgata tgccaaccat aagccacgtg 1860
acggtgaata atgttcttct ttacaaccgt cagctgaatg ccgaggagat caggaccttg 1920
ttcttgagcc aggacctgat tggcacggaa gcacacatgg gcagcagcag cggcagcagt 1980
gaaagaagta cgcccGGATC CGGCTGCTAA                                 2010
```

Figure 4.
SEQ ID NO:4

```
Met Gly Ser Ser His His His His His His Ser Ser Gly Leu Val Pro Arg Gly Ser His
1               5                   10                  15                  20
Met Ala Pro Gly Ser Ser Arg Val Glu Leu Phe Lys Arg Gln Ser Ser Lys Val Pro Phe
                25                  30                  35                  40
Glu Lys Gly Gly Lys Val Thr Glu Arg Val Val His Ser Phe Arg Leu Pro Ala Leu Val
                45                  50                  55                  60
Asn Val Asp Gly Val Met Val Ala Ile Ala Asp Ala Arg Tyr Glu Thr Ser Asn Asp Asn
                65                  70                  75                  80
Ser Leu Ile Asp Thr Val Ala Lys Tyr Ser Val Asp Asp Gly Glu Thr Trp Glu Thr Gln
                85                  90                  95                  100
Ile Ala Ile Lys Asn Ser Arg Ala Ser Ser Val Ser Arg Val Val Asp Pro Thr Val Ile
                105                 110                 115                 120
Val Lys Gly Asn Lys Leu Tyr Val Leu Val Gly Ser Tyr Asn Ser Ser Arg Ser Tyr Trp
                125                 130                 135                 140
Thr Ser His Gly Asp Ala Arg Asp Trp Asp Ile Leu Leu Ala Val Gly Glu Val Thr Lys
                145                 150                 155                 160
Ser Thr Ala Gly Gly Lys Ile Thr Ala Ser Ile Lys Trp Gly Ser Pro Val Ser Leu Lys
                165                 170                 175                 180
Glu Phe Phe Pro Ala Glu Met Glu Gly Met His Thr Asn Gln Phe Leu Gly Gly Ala Gly
                185                 190                 195                 200
Val Ala Ile Val Ala Ser Asn Gly Asn Leu Val Tyr Pro Val Gln Val Thr Asn Lys Lys
                205                 210                 215                 220
Lys Gln Val Phe Ser Lys Ile Phe Tyr Ser Glu Asp Glu Gly Lys Thr Trp Lys Phe Gly
                225                 230                 235                 240
Glu Gly Arg Ser Asp Phe Gly Cys Ser Glu Pro Val Ala Leu Glu Trp Glu Gly Lys Leu
                245                 250                 255                 260
Ile Ile Asn Thr Arg Val Asp Tyr Arg Arg Arg Leu Val Tyr Glu Ser Ser Asp Met Gly
                265                 270                 275                 280
Asn Ser Trp Val Glu Ala Val Gly Thr Leu Ser Arg Val Trp Gly Pro Ser Pro Lys Ser
                285                 290                 295                 300
Asn Gln Pro Gly Ser Gln Ser Ser Phe Thr Ala Val Thr Ile Glu Gly Met Arg Val Met
                305                 310                 315                 320
Leu Phe Thr His Pro Leu Asn Phe Lys Gly Arg Trp Leu Arg Asp Arg Leu Asn Leu Trp
                325                 330                 335                 340
Leu Thr Asp Asn Gln Arg Ile Tyr Asn Val Gly Gln Val Ser Ile Gly Asp Glu Asn Ser
                345                 350                 355                 360
Ala Tyr Ser Ser Val Leu Tyr Lys Asp Asp Lys Leu Tyr Cys Leu His Glu Ile Asn Ser
                365                 370                 375                 380
Asn Glu Val Tyr Ser Leu Val Phe Ala Arg Leu Val Gly Glu Leu Arg Ile Ile Lys Ser
                385                 390                 395                 400
Val Leu Gln Ser Trp Lys Asn Trp Asp Ser His Leu Ser Ser Ile Cys Thr Pro Ala Asp
                405                 410                 415                 420
Pro Ala Ala Ser Ser Ser Glu Arg Gly Cys Gly Pro Ala Val Thr Thr Val Gly Leu Val
                425                 430                 435                 440
Gly Phe Leu Ser His Ser Ala Thr Lys Thr Glu Trp Glu Asp Ala Tyr Arg Cys Val Asn
                445                 450                 455                 460
Ala Ser Thr Ala Asn Ala Glu Arg Val Pro Asn Gly Leu Lys Phe Ala Gly Val Gly Gly
                465                 470                 475                 480
Gly Ala Leu Trp Pro Val Ser Gln Gln Gly Gln Asn Gln Arg Tyr His Phe Ala Asn His
                485                 490                 495                 500
Ala Phe Thr Leu Val Ala Ser Val Thr Ile His Glu Val Pro Ser Val Ala Ser Pro Leu
                505                 510                 515                 520
Leu Gly Ala Ser Leu Asp Ser Ser Gly Gly Lys Lys Leu Leu Gly Leu Ser Tyr Asp Glu
                525                 530                 535                 540
Lys His Gln Trp Gln Pro Ile Tyr Gly Ser Thr Pro Val Thr Pro Thr Gly Ser Trp Glu
                545                 550                 555                 560
Met Gly Lys Arg Tyr His Val Val Leu Thr Met Ala Asn Lys Ile Gly Ser Val Tyr Ile
                565                 570                 575                 580
Asp Gly Glu Pro Leu Glu Gly Ser Gly Gln Thr Val Val Pro Asp Gly Arg Thr Pro Asp
                585                 590                 595                 600
Ile Ser His Phe Tyr Val Gly Gly Tyr Gly Arg Ser Asp Met Pro Thr Ile Ser His Val
                605                 610                 615                 620
Thr Val Asn Asn Val Leu Leu Tyr Asn Arg Gln Leu Asn Ala Glu Glu Ile Arg Thr Leu
                625                 630                 635                 640
Phe Leu Ser Gln Asp Leu Ile Gly Thr Glu Ala His Met Gly Ser Ser Ser Gly Ser Ser
                645                 650                 655                 660
Glu Arg Ser Thr Pro Gly Ser Gly Cys
                665
```

COMPOSITIONS FOR PROMOTING WOUND HEALING AND TREATING PSORIASIS

PRIORITY CLAIM

This application is a continuation-in-part of U.S. patent application Ser. No. 10/952,003, filed Sep. 28, 2004 now U.S. Pat. No. 7,335,638, which is a continuation-in-part of International Patent Application No. PCT/BR03/00049, filed Mar. 28, 2003 and published in English on Oct. 9, 2003 as WO 03/082324 (priority to both Ser. No. 10/952,003 and PCT/BR03/0049 being claimed herein), and further claims priority to U.S. Provisional Application Ser. No. 60/890,980, filed Feb. 21, 2007, all three of which are incorporated by reference in their entireties herein.

1. INTRODUCTION

The present invention relates to compositions and methods for promoting healing of cutaneous, mucosal and/or mucocutaneous lesions by topical application of a protein capable of removing sialic acid residues and a plant extract comprising nucleic acid containing particles.

2. BACKGROUND

Mycoplasmas represent some of the smallest self-replicating microorganisms, and have unique properties among the prokaryotes. These properties include the need for cholesterol to maintain their membrane envelope, and the absence of an external wall. Mycoplasmas are known to cause pulmonary infection in humans, and it is widely known that mycoplasmas can cause disease in most animals including humans as well as animals of commercial importance such as cattle, swine, and fowl. (Razin et al., 1998, Microbiol. and Molecular Biology Review, 62(4):1094-1156; Maniloff et al. Eds., 1992, Mycoplasmas, Molecular Biology and Pathogenesis, American Society for Microbiology, Washington).

Frequent co-occurrence of mycoplasma with other microorganisms, such as chlamydia, has been observed in diseases involving cell proliferation (International Patent Application No. PCT/BR01/00083, filed Jul. 3, 2001 and BR PI 0002989-0, filed Jul. 3, 2001). This association appears to increase the virulence of both pathogens. Mycoplasmal lipoproteins are potent macrophage activators and have a comparable activity and distribution in mollicutes as the LPS of Gram-negative bacteria. (Razin et al. Eds., 2002, Molecular biology and pathogenicity of mycoplasmas, Kluwer Academic/Plenum Publishers, New York). Recently described toll-like receptors (TLR) in macrophages that are activated by products from pathogens such as mycoplasmal lipoproteins and LPS from bacteria have been demonstrated to be important for activation of the immune system and it appears that the efficacy of the immune response depends on which concomitant TLR s are activated. (Akira et al., 2001, Nature Immunol. 2:675-680).

Archaea are the most ancient microorganisms existing in nature, but have been characterized only recently. See, Woese et al., Proc Natl. Acad. Sci. U.S.A. 74: 5088-5090 (1977). They inhabit extreme environments and are constituted by lipid monolayer membranes. Rich alkaline atmosphere with sodium ions and metals prevents proliferation of other bacteria, but is favorable to archaea's growth. Archaea have been isolated from alkaline waters from the Dead Sea, the Great Salt Lake and Yellowstone National Park. They have a small size, can—just barely—be viewed with an optical microscope, and observation of structural details requires electron microscopy. See, Howland et al., The surprising archaea. Discovering another domain of life, Oxford University Press (New York, 2000). Some are considered hyperthermophilic as they survive in very high temperatures.

Another unusual characteristic of some archaea is that they appear to use metal as an energy source. See, Amend et al., F. E. M. S. Microbiol. Rev. 25: 175-243 (2001). It is considered that archaea usually need an anaerobic or nearly anaerobic environments to carry out oxidation-reduction reactions with participation of different chemical compounds, including metals.

Recently, a new kind of extremely small archaea, which is dependent on bigger archaea, was described and named nanoarchaea. See, Huber J et al., Nature 417: 63-67 (2002). With the exception of archaea that reside in the mammalian intestine and produce methane gases, there is no report of archaea existing within plants or animals. See, Florin T H J et al., Am. J. Gastroenterol. 95: 2872-2879 (2000).

Cutaneous lesions, for example, psoriasis and radiodermatitis resulting from radiotherapy, present obstacles to successful wound healing, as the lesions result from continued exposure to causative factors such as radiation therapy for cancer, or immune system dysfunction in psoriasis. In particular, the persistence of radiodermatitis lesions often requires the suspension of radiation therapy during cancer treatment in order to permit healing of the lesions. Such interruptions can be detrimental to the successful treatment of cancer.

3. SUMMARY OF THE INVENTION

The present invention relates to compositions and methods for promoting healing of cutaneous, mucosal and/or mucocutaneous lesions by topical application of a protein capable of removing sialic acid residues and a plant extract comprising nucleic acid containing particles. In various embodiments of the invention, the composition is a topical gel, cream, or ointment comprising a protein capable of removing sialic acid residues, such as a neuraminidase enzyme and/or a trans-sialidase enzyme, and one or more purified plant extracts. In additional embodiments, the composition further comprises a metal chelator. Administration of the topical formulation to the lesion promotes healing.

4. BRIEF DESCRIPTION OF THE DRAWINGS

FIGS. 1A-F shows a decrease in edema and redness of radiodermatitis skin lesions following treatment with a trans-sialidase gel and an orchid extract gel. FIGS. 1A-C show three different patients presenting radiodermatitis degree 4, represented by inflammation and cutaneous ulcers (arrow) in a woman suffering from breast cancer (A), a woman with malignant melanoma (B) and a man with larynx cancer (C). FIG. 1D-F show the skin lesions of the same patients described in (A-C) following one week of treatment with trans-sialidase and orchid extract gels (arrow). The trans-sialidase gel was administered topically once per day to the lesions in an amount of 1.0 ml/50 $cm^2$ of cutaneous tissue each morning of treatment. The orchid extract gel was administered topically once per day to the lesions in an amount of 1.0 ml/50 $cm^2$ of cutaneous tissue each evening of treatment. The FIG. 2A-D shows lesions in a 59 year old woman suffering from psoriasis of the scalp before (A-B) and following (C-D) topical treatment with trans-sialidase and orchid extract gels. (A-B) show psoriatic lesions (arrows) characterized by silvery scales on bright red, well-demarcated plaques on the scalp. The plaques were usually associated with hair loss.

(C-D) show the same lesions as in A-B following two months of treatment with trans-sialidase and orchid extract gels. The trans-sialidase gel was administered topically once per day to the lesions in an amount of 1.0 ml/50 $cm^2$ of cutaneous tissue each morning of treatment. The orchid extract gel was administered topically once per day to the lesions in an amount of 1.0 ml/50 $cm^2$ of cutaneous tissue each evening of treatment.

FIG. 3 shows the nucleotide sequence of a plasmid encoding the catalytic trans-sialidase unit of trans-sialidase from *Trypanosoma cruzi* (SEQ ID NO:3). The letters in capital represent the pET14b plasmid and the underlined letters correspond to the position of the oligonucleotides used to amplify the *Trypanosoma cruzi* clone.

FIG. 4 shows the amino acid sequence of the protein encoded by the nucleic acid sequence depicted in FIG. 3. (SEQ ID NO:4). In bold are the amino acids not found in the original clone.

SEQUENCE LISTiNG

Figure 1:
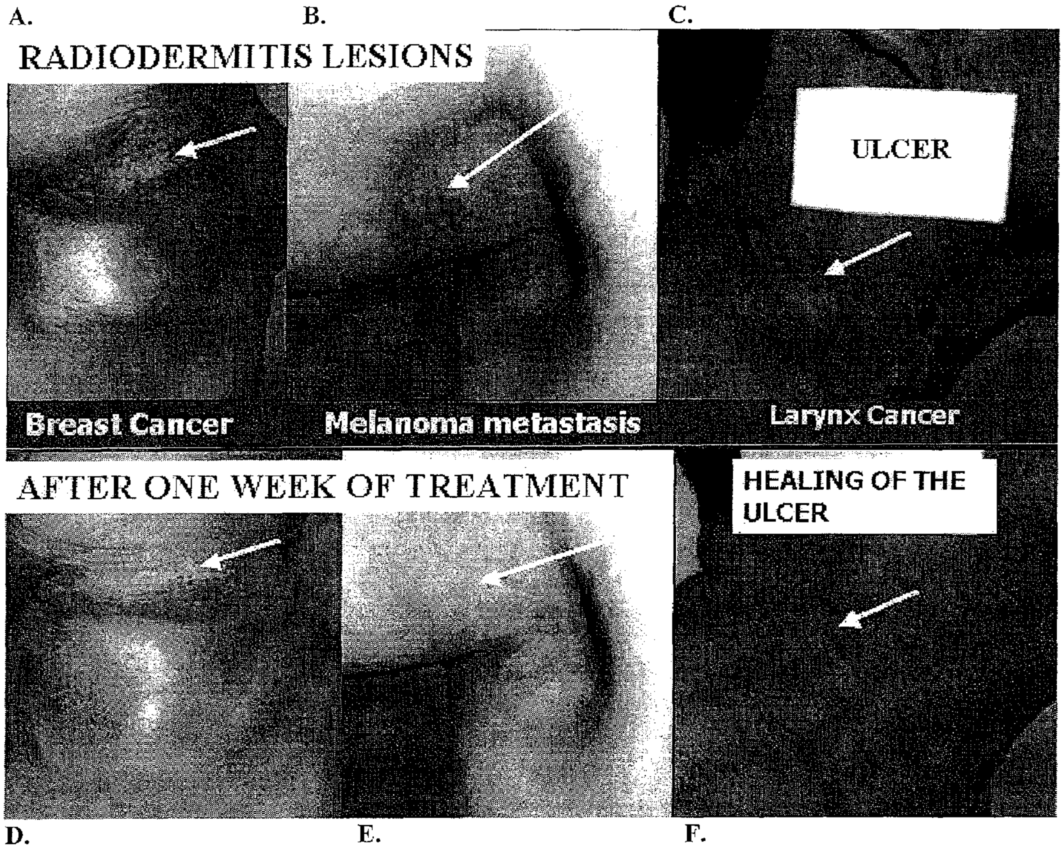

The specification further incorporates by reference the Sequence Listing submitted herewith via EFS on Nov. 4, 2008. Pursuant to 37 C.F.R. § 1.52(e)(5), the Sequence Listing text file, identified as 0685280111seqlist.txt, is 8,770 bytes and was created on Oct. 27, 2008. The Sequence Listing, electronically filed herewith, does not extend beyond the scope of the specification and thus does not contain new matter.

5. DETAILED DESCRIPTION OF THE INVENTION

For purposes of clarity, and not by way of limitation, the detailed description of the invention is divided into the following subsections:

(i) compositions for treating lesions; and (ii) methods of treatment.

5.1 Compositions for Treating Cutaneous Lesions

The present invention provides for compositions and methods that promote the healing of wounds, in particular, cutaneous, mucosal, and/or mucocutaneous lesions. Specifically, it has been found that the treatment of lesions with compositions of the invention promotes the healing of the lesions believed to be due to, without being bound to any particular theory, a decrease in the association of a mycoplasma and/or one or more non-mycoplasma microorganisms with the lesion being treated.

In non-limiting embodiments of the invention, the composition comprises a carrier, such as a gel, cream, ointment, or lotion which further comprises a protein capable of removing sialic acid residues, such as a neuraminidase enzyme, a trans-sialidase enzyme, or a combination thereof, and/or one or more purified plant extracts, and optionally, a metal chelator. According to the invention, application of the composition to a lesion inhibits or prevents the attachment of a mycoplasma and/or a non-mycoplasma microorganisms to the host cells.

The term "lesion" as described herein means any structural disturbance, defect or abnormality to the cuticle, skin, mucosa, or mucocutaneous tissues of a subject. Lesions include, for example, but not limited to, structural defects, for example, lacerations and surgical wounds, radiodermatitis or injury resulting from exposure to radiation, psoriasis, rashes, moles, cysts, pimples, warts, burns, irritations, abrasions, baldness, seborreic keratosis, keloid scars, chronic dermatitis, fibrosis, sclerosis, cutaneous thickening, scars, cutaneous discontinuities, and ulcers.

The term "composition," as used herein means one or more agents or combinations thereof effective to promote the healing of a lesion and/or decrease the presence of a mycoplasma and non-mycoplasma microorganism with the lesion. In one embodiment, the composition inhibits the ability of the mycoplasma and non-mycoplasma to associate with a substrate, for example, but not limited to, a lesion. In another non-limiting embodiment, the composition inhibits the association of a mycoplasma and a non-mycoplasma microorganism.

The term "carrier," as used herein means any agent the composition is mixed with to facilitate topical administration of the composition to a subject. Examples of carriers include, but is not limited to, gels, creams, ointments, liquids, or powders. In a preferred embodiment, the carrier is a gel.

The term "mycoplasma" as used herein means a microorganism of the genus *Mycoplasma* such as, but not limited to, *Mycoplasma (M.) buccale, M. faucium, M. fermentans, M. genitalium, M. hominis, M. lipophilum, M. oral, M. penetrans, M. pneumoniae, M. salivarium*, or *M. spermatophilum*. The one or more additional non-mycoplasma microorganism may be a bacteria, archaea or virus, for example, but not limited to, spirochete or chlamydia such as *Chlamydia pneumoniae*. According to the invention, the mycoplasma and non-mycoplasma may be attached to a substrate, for example, but not limited to, a lesion. In a further non-limiting embodiment, the mycoplasma and non-mycoplasma are attached to the substrate by sialic acid.

In a preferred embodiment of the invention, the protein capable of removing sialic acid residues is a trans-sialidase or neuraminidase enzyme.

In certain non-limiting embodiments, the composition comprises a neuraminidase enzyme of, for example but not limited to, *Bacteroides fragilis, Streptococcus pneumoniae, Streptococcus oralis, Arthrobacter ureafaciens, Clostridium perfringens, Mycoplasma alligatoris, Arcanobacterium pyogenes, Clostridium sordellii, Pseudomonas aeruginosa, Micromonospora viridifaciens, Vibrio cholerae. Streptomyces avermitilis*, Influenza virus, *Streptomyces coelicolor, Flavobacteriales bacterium*, and *Solibacter usitatus.*

In another non limiting embodiment, the protein comprises a trans-sialidase, for example, the trans-sialidase enzyme of *Trypanosoma brucei.*

In a preferred embodiment of the invention, the composition comprises the trans-sialidase enzyme of *Trypanosoma cruzi*, or a portion or variant of the native enzyme which has trans-sialidase activity.

Alternatively, the trans-sialidase enzyme may be a recombinant trans-sialidase enzyme.

According to the invention, the recombinant trans-sialidase is as described in International Patent Publication WO/2002/002050 by Higuchi et al., published Jan. 10, 2002; and U.S. Pat. No. 7,108,851 by Higuchi et al., issued Sep. 19, 2006. For example, the trans-sialidase gene may be obtained from a genomic clone, isolated from a commercially available lambda Zap®II library (Stratagene, http://www.stratagene.com) of *T. cruzi* Y strain (Silva and Nussenzweig, 1953, Folia Clin Biol 20: 191-203), as described in Uemura et al. (Uemura et al., 1992, EMBO J 11: 3837-3844). From the original lambda clone, which expresses enzymatic activity, an SK plasmid containing the trans-sialidase gene may be generated (SK-154-0). The preferred plasmid used is pTSII, which corresponds to a fragment of the original gene (clone 154-0) amplified through PCR, and inserted into the sites NdeI and BamH1 of the vector pET14b (Novagen-http://www.novagen.com). The PCR product may be amplified using SK-154-0 as a template with the following primers:

```
a) TSPET14:
5'-GGAATTCCATATGGCACCCGGATCGAGC        (SEQ ID NO:1)

b) RT154:
5'-CGGATCCGGGCGTACTTCTTTCACTGGTGCCGGT  (SEQ ID NO:2)
```

The resulting PCR product should have a nucleic acid sequence as set forth in FIG. 3 (SEQ ID NO:3), and a corresponding amino acid sequence as depicted in FIG. 4 (SEQ ID NO:4). The resulting plasmid may be transformed into the *Escherichia coli* BLB21 DE3. The construct can be made in two steps due to an internal BamH1 site in the trans-sialidase gene. The PCR product may be treated with BamH1 and NdeI enzymes, and the resulting fragments fractionated by electrophoresis on an agarose gel. The separated fractions may then be purified from the gel with the Sephaglass purification kit (Amersham-Pharmacia). The 5' NdeI-BamH1 digestion fragment may be ligated into the pET14b vector which has been pre-digested with BamH1 and NdeI. The ligation products may be used to transform K12 DH5a *E. coli* cells. The plasmid containing *E. coli* cells may be selected and the plasmid purified by methods known in the art. The purified construct may be treated with BamH1, shrimp alkaline phosphatase, and ligated with the BamHI-BamHI-3' fragment purified from the fractionation gel. The ligation products may then be used to transform K12 DH5a *E. coli* cells, from which clones expression of trans-sialidase may be selected and purified. The final plasmid may be confirmed by restriction analysis and used to transform the BLB21 DE3 pLys strain of *E. coli*, from which recombinant trans-sialidase enzyme can be purified, as described in International Patent Publication WO/2002/002050 by Higuchi et al., published Jan. 10, 2002; and U.S. Pat. No. 7,108,851 by Higuchi et al., issued Sep. 19, 2006.

Alternatively, the trans-sialidase enzyme may be purified from a culture of *Trypanosoma cruzi*, such as, for example, a culture according to Kloetzel et al. (Kloetzel et al., 1984, Rev. Inst. Med. Trop. Sao Paulo., 26:179-85). Supernatant from the culture may be filtered through a 1 μm pore filter in a vacuum chamber. The enzyme may be further purified by filtering the supernatant through a 0.22 μm filter and then precipitating the filtrate with a 50% $(NH_4)2SO_4$ solution. The precipitates may then be dialyzed against phosphate-buffered saline, and passed through a tresyl-agarose column comprising an immobilized anti-trans-sialidase monoclonal or polyclonal antibody. The column may be washed with phosphate-buffered saline, followed by an additional wash with 10 mM sodium phosphate, pH 6.5. The trans-sialidase may then be eluted with a 3.5 mM $MgCl_2$, 10 mM sodium phosphate, pH 6.0 solution. The fractions eluted from the column may be filtered through a Sephadex G-25 column equilibrated with 20 mM Tris-HCl, pH 8.0, to remove the $MgCl_2$. The trans-sialidase may be further purified by passage through a Mono Q column equilibrated in 20 mM Tris-HCl, pH 8.0, and eluted with a linear gradient from 0 to 1 mM NaCl in the same buffer.

The purified enzyme derived from the culture should comprise 400 kDa multimeric aggregates. The enzymatic activity of the purified trans-sialidase may be measured according to methods described in International Patent Publication WO/2002/002050 by Higuchi et al., published Jan. 10, 2002; and U.S. Pat. No. 7,108,851 by Higuchi et al., issued Sep. 19, 2006.

In non-limiting embodiments, the purified trans-sialidase has an enzymatic activity of between 0.1 and 10 U/ml, more preferably between 1.0 and 5.0 U/ml, and most preferably 1.3 U/ml.

In a further non-limiting embodiments, the plant extract may be derived from, for example but not limited to, *Allium sativum* (garlic), *Ginkgo biloba*, tomato, orchid, guava, ginseng, for example *Pfaffia paniculata* (Brazilian ginseng); tobacco; or *Zingiber officinale* (ginger), wherein the orchid is preferably of the genus *Cymbidium*, for example, yellow or green orchids from the genus *Cymbidium* (*Cymbidium* ssp.). Alternatively, the orchid is of the genus *Dendrobium*, for example, *Dendrobium nobile* or *Dendrobium moschatum.*

The extract from plants may be obtained by adding a solvent, such as, for example, alcohol, to the plant tissue, for example, but not limited to, roots, cloves, flower petals, or leaves which may be chopped, or macerated prior to mixture with the solvent. The solvent may be mixed with the plant tissue in a proportion of between 1:99 and 60:40, more preferably between 15:85 and 50:50 and most preferably between 30-40:70-60 of plant mass:alcohol. The solvent can be an alcohol, for example, ethanol, methanol, or grain alcohol, and can have a concentration of between 60% and 100%, more preferably between 70% and 95%, and most preferably about 92% alcohol. The plant/alcohol mixture may be aged in a dark, anaerobic environment for a period of time between 15 days and 24 months, more preferably between 1 and 12 months, and most preferably 10 months.

According to the invention, the extract derived from plant comprises particles containing nucleic acid (DNA and/or RNA), wherein the particle is an archaea (preferably non-pathogenic) and/or a nanoarchaea, and further wherein the particle is present in an amount effective to prevent or inhibit the growth of a mycoplasma and one or more non-mycoplasma microorganisms. Aging of the plant/alcohol mixture increases the concentration of particles in the mixture.

The plant/alcohol mixture may be purified, and the concentration of nanoparticles may be increased through one or more filtrations. The mixture can be filtered through pores of between 0.5 μm and 50 μm, more preferably between 5 μm and 20 μm, and most preferably 11 μm, for example, but not limited to Whatman qualitative filter paper grade 1, diameter 24 cm, pore size 11 μm. Vacuum chambers can also be used separately, or in addition to other filtration methods. Additionally, glass microfiber filters can be used, for example, but not limited to, a 47 mm diameter glass microfiber filter with a pore size of 1.1 μm. Man filtration methods are known in the art can be used to filter the aged plant/alcohol mixture.

In a non-limiting embodiment, the plant/alcohol mixture can be subjected to additional aging during the filtration process. For example, olive oil may be added to the filtrate to create a 1% olive oil filtrate mixture, followed by an additional month of storage in a dark anaerobic environment.

Furthermore, the composition may comprise particles and/or nanoparticles containing DNA or RNA, wherein the particles are a non-pathogenic archaea and/or a nanoarchaea, and further wherein the particle is present in amounts effective to prevent or inhibit the growth of a mycoplasma and one or more non-mycoplasma microorganisms. The nanoparticles may be between 5-500 nm, more preferably between 15-250 nm, and most preferably between 30-150 nm in diameter. Alternatively, the composition may comprise medium particles of between 500 nm and 1.1 μm in diameter. Additionally, the compositions may comprise one or a combination of both small and medium particles. The size of a particle can enlarge or decrease depending on the concentration of water and ions in a solution comprising the particles, such as, for example, Na+or Ca+.

Figure 5:
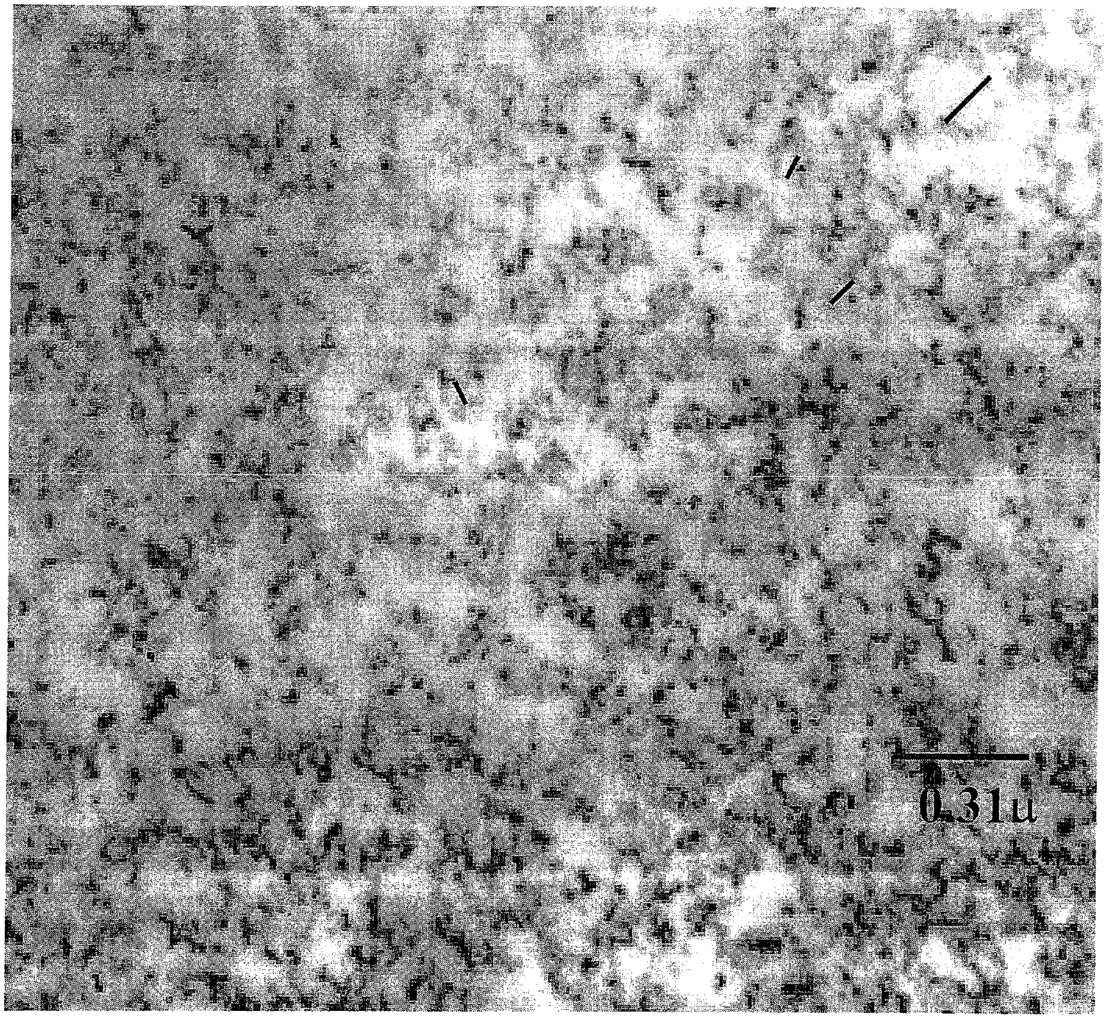
FIG. 5 shows small dark electron-dense nanoarchae of between 0.03-0.15 μm in diameter.
Figure 6:
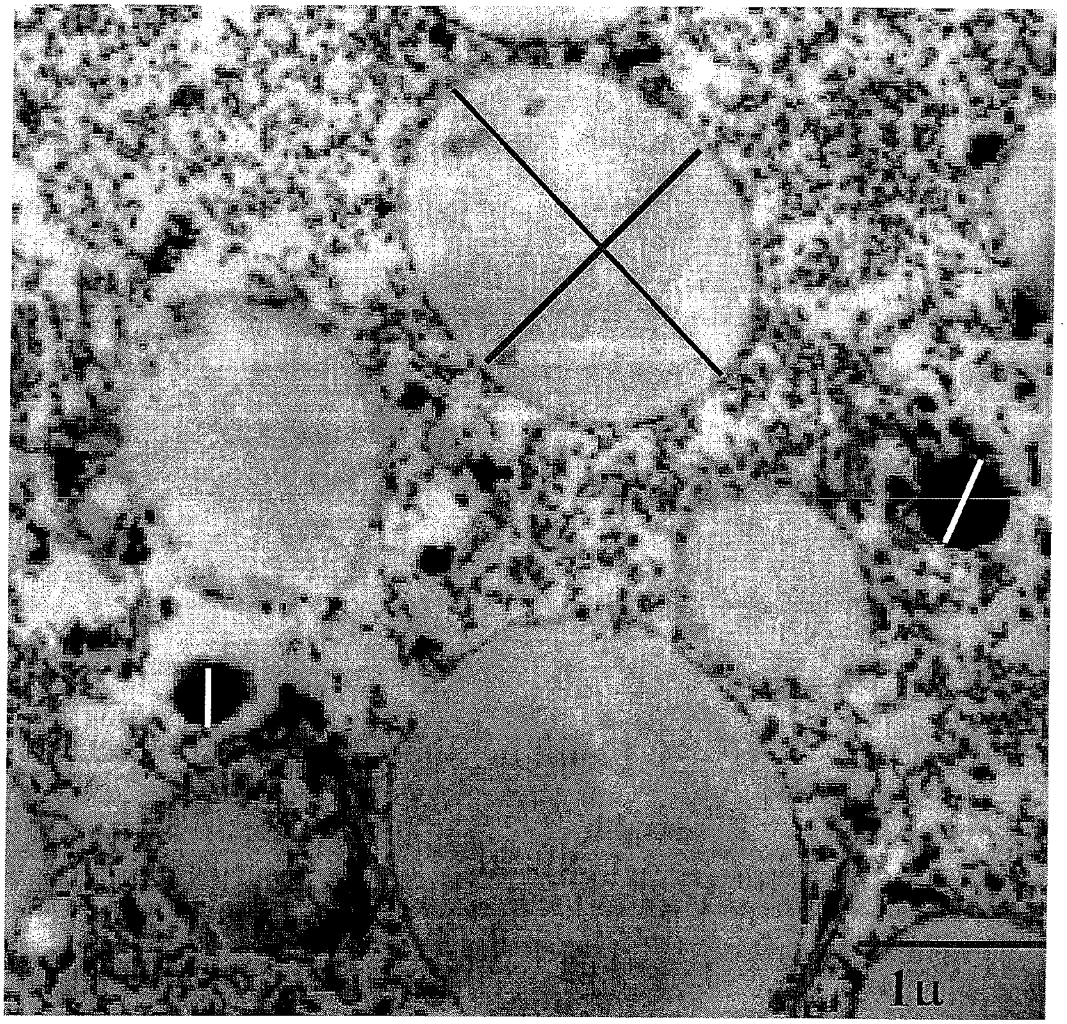
FIG. 6 shows dark medium sized electron-dense archaea of between 0.5-1.1 μm in diameter, and large clear, empty archaea of between 1.0-2.4 μm in diameter.
Figure 7:
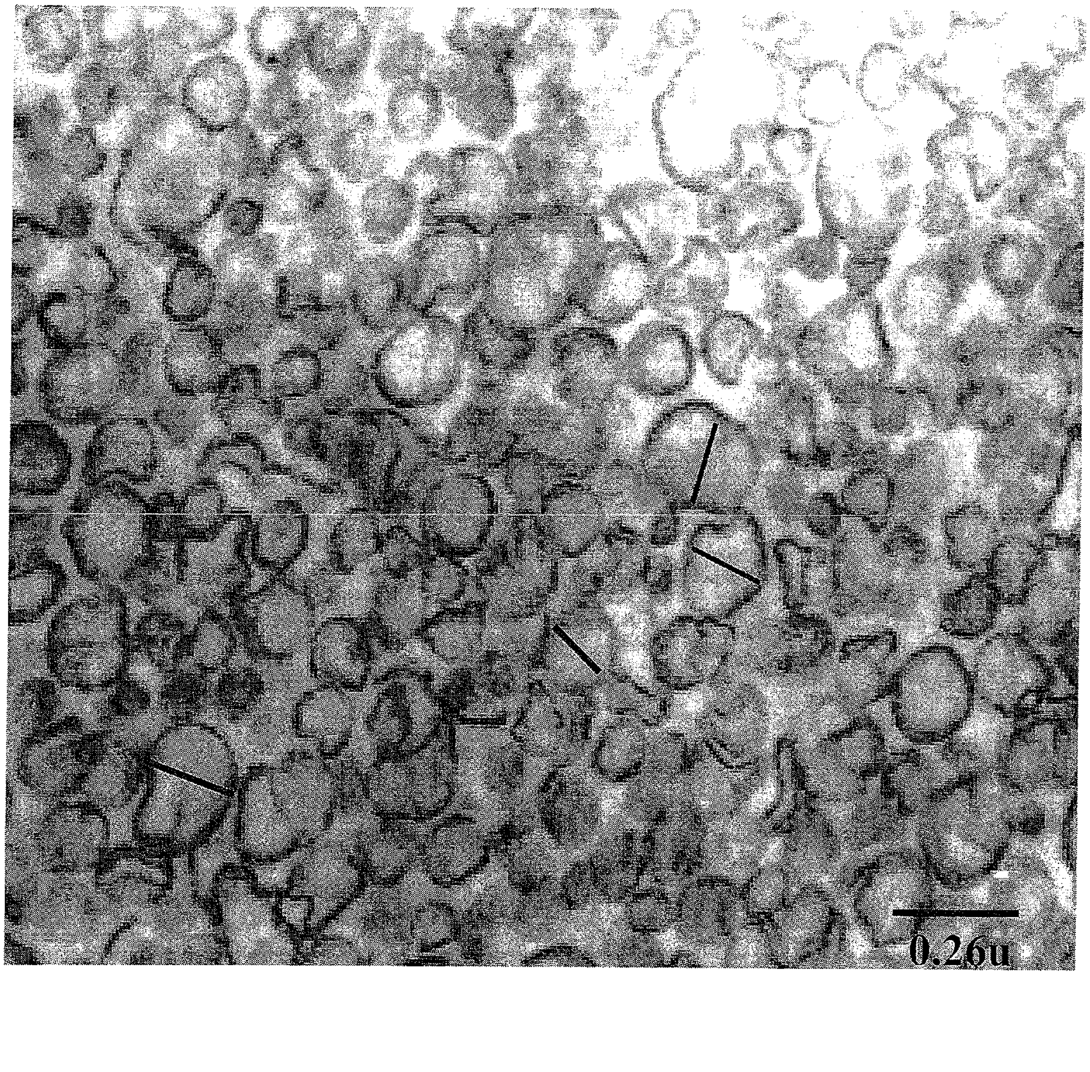
FIG. 7 shows clear, empty archaea of between 0.15-2.0 μm in diameter.

According to the invention, the purity of the plant extract may be determined by microscopic examination of the filtered, aged, plant extract, as described in U.S. Patent Application Publication No. 20050142116. For example, the filtered, aged plant extract can be stained with any DNA or RNA dye known in the art, such as acridine orange, bisbenzimide H 33342 (Hoechst), or 4',6-diamidino-2-phenylindole, dihydrochloride (DAPI); and viewed with an immunofluorescence optical microscope, an electron microscope, or any other microscope known in the art. Two forms of archaea, having different morphological characteristics may be identified. One type comprising an electron-dense content may be between about 0.03-0.15 μm (nanoparticle) and about 0.5-1.1 μm in diameter (medium particle) (FIGS. 5 and 6, respectively). A second type may comprises a clear, empty content, and may be about 0.15-2.4 μm in diameter (FIGS. 6 and 7). The clear, empty archaea are similar in morphology to the pathogenic archaea associated with lesions, while the electron dense archaea comprise the non-pathogenic archaea and nanoarchaea comprising DNA or RNA. Brilliant red particles, which may comprise metallic ions, may also adhere to the surface of the archaea. Optimum purity may be achieved when predominantly, preferably essentially, only fast moving electron-dense nanoparticles are visible. The presence of clear, empty archaea or large brilliant red particles of about 0.15-0.24 μm and at a concentration of, for example, ≧1.0 large brilliant red particle/visual field, indicates suboptimal purity. In cases of suboptimal purity, the filtered aged plant extract is subjected to additional filtration, for example, tangential flow filtration in the Minitan Ultrafiltration System (Millipore, Bedford, Mass., USA), using the microporous membrane packet (30,000 NMWL). In preferred embodiments, the compositions of the invention comprise a greater number of electron dense archaea (nanoparticles and medium particles) than empty, clear archaea; and a greater number of archaea not associated with large brilliant red particles than those associated with large brilliant red particles.

According to the invention, the purified plant extract may comprise an enriched population of particles. The concentration of particles maybe between $1\times10^5$ and $1\times10^{10}$ particles/ml, more preferably between $1\times10^6$ and $1\times10^9$ particles/ml, and most preferably about $1\times10^7$ particles/ml.

In certain non-limiting embodiments, the composition comprises a metal chelator, for example, but not limited to, Nitrilotriacetate (NTA), diphenylthiocarbazone(dithizone), histidine, the lipophilic metal chelator DP-109, ethylene glycol tetraacetic acid (EGTA), ethylenediaminetetraacetic acid (EDTA), DMPS (2,3-dimercapto-1-propanesulfonate), Lysinoalanine, Synthetic lysinoalanine (N-ε-DL-(2-amino-2-carboxyethyl)-L-lysine), tetracycline, alpha lipoic acid (ALA), Dimercaptosuccinic acid, (DMSA), 2,3-Dimercapto-1-propanesulfonic acid (DMPS), Calcium disodium versante ($CaNa_2$-EDTA), D-penicillamine, Deferoxamine, Defarasirox, Dimercaprol (BAL), the calcium salt of diethylene triamine pentaacetic acid (DTPA), or any other metal chelator known in the art. In a preferred embodiment, the metal chelator is pyrrolidine dithiocarbamate (PDTC). In a preferred embodiment, the metal chelator is pyrrolidine dithiocarbamate (PDTC). The composition of the invention may comprise the metal chelator in a concentration of between about 0.01 and 10 mg/ml, more preferably between about 0.5 and 5 mg/ml, more preferably between about 1 and 2 mg/ml, and most preferably about 1.5 mg/ml.

In a non-limiting embodiment, the compositions of the invention comprise combinations of trans-sialidase, a metal chelator, and one or more purified plant extracts as shown in Table I.

TABLE I

| Combinations of trans-sialidase, a metal chelator, and one or more purified plant extracts encompassed by the invention. Combinations of trans-sialidase (TS), pyrrolidine dithiocarbamate (PDTC), and purified plant extracts |
|---|
| TS |
| TS + PDTC |
| TS + PDTC + *Allium sativum* (AS) |
| TS + PDTC + *Ginkgo biloba* (GB) |
| TS + PDTC + *Zingiber officinale* (ZO) |
| TS + PDTC + orchid extract (OE) |
| TS + PDTC + AS + GB |
| TS + PDTC + AS + ZO |
| TS + PDTC + AS + OE |
| TS + PDTC + AS + GB + ZO |
| TS + PDTC + AS + GB + OE |
| TS + PDTC + AS + GB + ZO + OE |
| TS + PDTC + AS + ZO + OE |
| TS + PDTC + GB + ZO |
| TS + PDTC + GB + OE |
| TS + PDTC + GB + ZO + OE |
| TS + PDTC + ZO + OE |
| TS + AS |
| TS + GB |
| TS + ZO |
| TS + OE |
| TS + AS + GB |
| TS + AS + ZO |
| TS + AS + OE |
| TS + AS + GB + ZO |
| TS + AS + GB + OE |
| TS + AS + GB + ZO + OE |
| TS + AS + ZO + OE |
| TS + GB + ZO |
| TS + GB + OE |
| TS + GB + ZO + OE |
| TS + ZO + OE |

5.2 Methods of Treatment

The present invention provides for compositions and methods that promote the healing of wounds, in particular, cutaneous, mucosal, and/or mucocutaneous lesions. Specifically, it has been found that the treatment of lesions with compositions of the invention promotes the healing of the lesions believed to be due to, without being bound to any particular theory, a decrease in the association of a mycoplasma and/or one or more non-mycoplasma microorganisms with the lesion being treated. In a non-limiting embodiment of the invention, the composition may be administered topically to a lesion as a lotion, cream, liquid, paste, ointment, powder, or any other carrier known in the art. In a preferred embodiment of the invention, the composition is applied as a topical gel.

In one non-limiting embodiment, the composition of the invention is applied in an amount effective to promote healing of wounds, in particular, cutaneous, mucosal, and/or mucocutaneous lesions, for example, but not limited to, structural defects, for example, lacerations and surgical wounds, radiodermatitis or injury resulting from exposure to radiation, psoriasis, rashes, moles, cysts, pimples, warts, burns, irritations, abrasions, baldness, seborreic keratosis, keloid scars, chronic dermatitis, fibrosis, sclerosis, cutaneous thickening, scars, cutaneous discontinuities, and ulcers.

The term "treatment" as defined herein means a reduction in lesion size, inflammation, irritation, scaling, scar formation, fibrosis, sclerosis, and cutaneous thickening. In a non-limiting embodiment, the treatment may reduce the presence of moles, cysts, pimples, warts, burns, irritations, abrasions, baldness, seborreic keratosis, keloid scars, chronic dermatitis, cutaneous discontinuities, structural defects, lacerations and surgical wounds.

In a non-limiting embodiment, the methods and compositions of the invention are effective for treating a lesion, wherein topical administration of the composition may be effective to reduce the size of the lesion by at least about 1%, 5%, 10%, 25%, 50%, 75%, 90%, or 100%.

The present invention provides for formulations, to be applied topically to a cutaneous, mucous, or mucocutneous lesion. The composition may comprise between about $1\times10^{-8}$ and $1\times10^{-4}$ U/ml, or between about $1\times10^{-7}$ and $1\times10^{-5}$ U/ml, or between about $1\times10^{-6}$ and $5\times10^{-6}$ U/ml, and most preferably about $2\times10^{-6}$ U/ml of neuramidase and/or trans-sialidase activity. The composition may also comprise between about 100 and $1\times10^{7}$ plant extract derived particles/ml, or between about $1\times10^{3}$ and $1\times10^{6}$ particles/ml, or between about $1\times10^{4}$ and $5\times10^{5}$ particles/ml and most preferably about $3\times10^{5}$ particles/ml. Optionally, the composition may comprise a metal chelator, for example, but not limited to, PDTC, NTA, diphenylthiocarbazone(dithizone), histidine, DP-109, EGTA, EDTA, DMPS, Lysinoalanine, Synthetic lysinoalanine, tetracycline, ALA, Dimercaptosuccinic acid, DMSA, Calcium disodium versante, D-penicillamine, Deferoxamine, Defarasirox, Dimercaprol, or DTPA, in a concentration of between about 0.01 and 10 mg/ml, or between about 0.5 and 5 mg/ml, or between about 1 and 2 mg/ml, and most preferably about 1.5 mg/ml.

In specific non-limiting embodiments, the composition comprises $2.6\times10^{-6}$ U/ml neuramidase and/or trans-sialidase activity, and/or $3\times10^{5}$ plant derived particles/ml.

Alternatively, the composition may comprise between about 0.01 and 10 U/ml, or between about 0.2 and 5 U/ml, or between about 0.5 and 2 U/ml and most preferably about 1.0 U/ml of neuramidase and/or trans-sialidase activity.

In one embodiment of the invention, the gel is a trans-sialidase gel, wherein the trans-sialidase gel is created by mixing trans-sialidase enzyme with a gel, for example, but not limited to, a non-ionic, anionic, or cationic gel. In one preferred embodiment, the gel is a hydroxyethylcellulose gel, for example, Natrosol® gel The trans-sialidase enzyme may be diluted with a suitable dilutant, for example, but not limited to, MilliQ purified water, distilled water, or thermal water, prior to mixing with the carrier. In a preferred embodiment, the dilutant is MilliQ purified water . When diluted, the trans-sialidase is diluted at a trans-sialidase:dilutant ratio of between 1:1 and 1:2,000,000, more preferable between 1:100 and 1:1,000,000, more preferably between 1:1000 and 1:500,000, and most preferably 1:250,000. The resulting trans-sialidase dilution, or alternatively, undiluted enzyme, may then be mixed with a gel at a trans-sialidase:gel ratio of between 1:1000 and 1000:1, more preferably between 1:100 and 100:1, more preferably between 1:10 and 10:1 and most preferably 1:1.

In one, non-limiting example, the trans-sialidase gel is made by diluting a purified trans-sialidase enzyme 1:250,000 in purified water, for example, MilliQ purified water. The diluted trans-sialidase is then mixed into Natrosol® gel (Dermavita, Brusque, Santa Catarina, Brazil), at a concentration of 1:1 and stored at 4° C. The gel may be applied topically to a subject in an amount of 1.0 ml/50 $cm^2$ of cutaneous surface.

In one non-limiting embodiment of the invention, the trans-sialidase enzymatic activity of the trans-sialidase gel is between 100 and 100,000 CPM, more preferably between 1000 and 20,000 CPM, more preferably between 1,500 and 10,000 CPM, and most preferably between 2,000-5,000 CPM, wherein 30,000 CPM corresponds to 0.36 nmoles of transferred sialic acid in a 30 min assay, which is further defined as one (1) unit (U).

In a non-limiting embodiment of the invention, the trans-sialidase gel may be administered topically to a subject in need of treatment, wherein the gel is administered one or more times per day. For example, the trans-sialidase gel may be administered once, twice, three, four, five, or 6 or more times per day. In a non-limiting example, the trans-sialidase gel may be applied topically once per day in the morning or evening during treatment.

In another non-limiting embodiment, the gel is a purified plant extract gel, preferably an orchid extract gel. The purified plant extract may be diluted with a suitable dilutant, for example, but not limited to, MilliQ purified water, distilled water, or thermal water, prior to mixing with the carrier. When diluted, the purified plant extract is diluted at a plant extract:dilutant ratio of between 1:100 and 100:1, more preferably between 1:50 and 50:1, more preferably between 1:10 and 10:1, and most preferably 1:5. The diluted or undiluted purified plant extract may be mixed with a gel, for example, but not limited to, an anionic gel. In a preferred embodiment, the gel is a hydroxyethylcellulose gel, for example, Natrosol® gel.

In a further non-limiting embodiment, the gel and the diluted or undiluted purified plant extract are mixed to achieve a gel with a final plant extract concentration of between 0.1% and 99%, more preferably between 5% and 80%, more preferably between 10% and 50%, and most preferably 15%.

In a non-limiting example, the purified plant extract is diluted 1:5 in thermal water (e.g. from Irai-RS, Brazil, or another thermal water source), which was previously boiled and filtered. The diluted plant extract is then mixed with an anionic gel (Dennavita, Brusque, Santa Catarina, Brazil; or another thermal water source) until the mixture achieved a final concentration of 15% plant extract. The gel may be applied typically to a subject in an amount of 1.0 ml/50 $cm^2$ of cutaneous surface.

In a non-limiting embodiment of the invention, the purified plant extract gel may be administered topically to a subject in need of treatment, wherein the gel is administered one or more times per day. For example, the purified plant extract gel may be administered once, twice, three, four, five, or 6 or more times per day. In a non-limiting example, the purified plant extract gel may be applied topically once per day in the morning or evening during treatment.

In another non-limiting embodiment of the invention, both the purified plant extract gel and the trans-sialidase gel may be administered topically to a subject in need of treatment, wherein the gels are administered one or more times per day, for example, the purified plant extract gel and the trans-sialidase gel may be administered once, twice, three, four, five, or 6 or more times per day. In a further non-limiting embodiment, the purified plant extract gel and the trans-sialidase gel may be administered simultaneously or in series. In a non-limiting example, the trans-sialidase gel may be applied topically once per day in the morning and the purified plant extract gel may be applied topically once per day in the evening during treatment. Alternatively, the gels may be applied topically at the same time.

In an additional non-limiting embodiment of the invention, the composition comprises both trans-sialidase and one or more purified plant extracts, for example, a gel comprising both a trans-sialidase gel and a purified plant extract gel. The two gels may be combined to produce a gel with a final trans-sialidase gel:purified plant extract gel ratio of between about 99:1 and 1:99, more preferably between 90:10 and 10:90, more preferably between 85:15 and 15:85, and most preferably 80:20.

The gel mixture comprising both the trans-sialidase gel and the purified plant extract gel may comprise a trans-sialidase enzymatic activity of between about $1\times10^{-8}$ and 1x10−4 U/ml, or between about $1\times10^{-7}$ and $1\times10^{-5}$ U/ml, or between about $1\times10^{-6}$ and $5\times10^{-6}$ U/ml, and preferably about $2\times10^{-6}$ U/ml. The gel mixture may further comprises between about 100 and $1\times10^{7}$ plant extract derived particles/ml, or between about $1\times10^{3}$ and $1\times10^{6}$ particles/ml, or between about $1\times10^{4}$ and $1\times10^{5}$ particles/ml and preferably about $6\times10^{4}$ particles/ml.

In a specific, non-limiting embodiment, the gel comprises both a trans-sialidase enzymatic activity of 2.08 U/ml and $6\times10^{4}$ plant derived particles/ml.

In a non-limiting embodiment, the gel comprising both trans-sialidase and one or more purified plant extracts may be administered topically to a subject in need of treatment, wherein the gel is administered one or more times per day. For example, the gel may be administered once, twice, three, four, five, or 6 or more times per day. In a non-limiting example, the gel may be applied topically once per day in the morning or evening during treatment.

In a non-limiting embodiment of the invention, the composition is applied to a lesion in an amount between about 0.1 ml/50 $cm^2$ and 100 ml/50 $cm^2$, or between about 0.5 ml/50 $cm^2$ and 50 ml/50 $cm^2$, and most preferably about 1.0 ml/50 $cm^2$ of cutaneous surface.

In an alternative embodiment, the composition is applied to the lesion in an amount between about 0.1 ml/5 $cm^2$ and 100 ml/5 $cm^2$, or between about 0.5 ml/5 $cm^2$ and 50 ml/5 $cm^2$, and most preferably about 1.0 ml/5 $cm^2$ of cutaneous surface.

In a non-limiting example, the methods and compositions of the invention may be effective for treating radiodermatitis lesions. Daily topical administration of the trans-sialidase gel once per day in the morning, and the purified plant extract gel once per day in the evening during a treatment period which may be between one week, two weeks, one month, two months, or three months and one year may be effective to reduce the lesions. The gels may be administered in an amount of between about 1.0 ml/5 $cm^2$ and 1.0 ml/50 $cm^2$, or between about 1.0 ml/5 $cm^2$ and 50 ml/50 $cm^2$, or between about 1.0 ml/5 $cm^2$ and 100 ml/50 $cm^2$, wherein the trans-sialidase gel comprises an enzymatic activity of between about $1\times10^{-8}$ and $1\times10^{-4}$ U/ml, or between about $1\times10^{-7}$ and $1\times10^{-5}$ U/ml, or between about $1\times10^{-6}$ and $5\times10^{-6}$ U/ml, and preferably about $2.6\times10^{-6}$ U/ml. The purified plant extract gel may comprise between about 100 and $1\times10^{7}$ plant extract derived particles/ml, or between about $1\times10^{3}$ and $1\times10^{6}$ particles/ml, or between about $1\times10^{4}$ and $5\times10^{5}$ particles/ml and preferably about $3\times10^{5}$ particles/ml. Alternatively, the gel may be a mixture of both the trans-sialidase gel and the purified plant extract gel wherein the gel mixture comprises a trans-sialidase enzymatic activity of between about $1\times10^{-8}$ and $1\times10^{-4}$ U/ml, or between about $1\times10^{-7}$ and $1\times10^{-5}$ U/ml, or between about $1\times10^{-6}$ and $5\times10^{-6}$ U/ml, and preferably about $2.08\times10^{-6}$ U/ml, and further wherein the gel mixture comprises between about 100 and $1\times10^{7}$ plant extract derived particles/ml, or between about $1\times10^{3}$ and $1\times10^{6}$ particles/ml, or between about $1\times10^{4}$ and $1\times10^{5}$ particles/ml and preferably about $6\times10^{4}$ particles/ml.

The treatment may be administered between intervals of radiation treatment for cancer. Such treatment may be effective to reduce the size of radiodermatitis lesions by about 1%, 5%, 10%, 25%, 50%, 75%, 90%, or 100%.

In another non-limiting example, the methods and compositions of the invention may be effective for treating psoriasis. Daily topical administration of the trans-sialidase gel once per day in the morning, and the purified plant extract gel once per day in the evening during a treatment period which may be between one week, two weeks, one month, two months, or three months and one year may be effective to reduce the psoriatic lesions. The gels may be administered in an amount of between about 1.0 ml/5 $cm^2$ and 1.0 ml/50 $cm^2$, or between about 1.0 ml/5 $cm^2$ and 50 ml/50 $cm^2$, or between about 1.0 ml/5 $cm^2$ and 100 ml/50 $cm^2$, wherein the trans-sialidase gel comprises an enzymatic activity of between about $1\times10^{-8}$ and $1\times10^{-4}$ U/ml, or between about $1\times10^{-7}$ and $1\times10^{-5}$ U/ml, or between about $1\times10^{-6}$ and $5\times10^{-6}$ U/ml, and preferably about $2.6\times10^{-6}$ U/ml. The purified plant extract gel may comprise between about 100 and $1\times10^{7}$ plant extract derived particles/ml, or between about $1\times10^{3}$ and $1\times10^{6}$ particles/ml, or between about $1\times10^{4}$ and $5\times10^{5}$ particles/ml and preferably about $3\times10^{5}$ particles/ml. Alternatively, the gel may be a mixture of both the trans-sialidase gel and the purified plant extract gel wherein the gel mixture comprises a trans-sialidase enzymatic activity of between about $1\times10^{-8}$ and $1\times10^{-4}$ U/ml, or between about $1\times10^{-7}$ and $1\times10^{-5}$ U/ml, or between about $1\times10^{-6}$ and $5\times10^{-6}$ U/ml, and preferably about $2.08\times10^{-6}$ U/ml, and further wherein the gel mixture comprises between about 100 and $1\times10^{7}$ plant extract derived particles/ml, or between about $1\times10^{3}$ and $1\times10^{6}$ particles/ml, or between about $1\times10^{4}$ and $1\times10^{5}$ particles/ml and preferably about $6\times10^{4}$ particles/ml.

The treatment may be administered between intervals of radiation treatment for cancer. Such treatment may be effective to reduce the size of radiodermatitis lesions by about 1%, 5%, 10%, 25%, 50%, 75%, 90%, or 100%.

6. EXAMPLES

Example 1

Treat of Radiodermatitis and Inflamed Cutaneous Lesions

In the following study, thirty-one patients presenting severe skin lesions caused by radiodermatitis after radiotherapy were treated with daily topical application of a trans-sialidase gel and an orchid gel to the lesions. Application of the gels decreased the edema and redness of the radiodermatitis lesions.

Materials and Methods

Production of Purified Plant Extract

Orchid flowers, *Cymbidium* ssp., *Dendrobium nobile* and *Dendrobium moschatum* were immersed whole in 92% ethanol, in a 30:70 proportion plant weight:ethanol. The mixture was stored in a dark, anaerobic environment (in a sealed bottle), for at least 10 months. Following storage, the mixture was passed through Whatman qualitative filter paper grade 1, diameter 24 cm, pore size 11 μm. Olive oil was then added at a volume of 10 ml per 1000 ml of the filtrate and stored for at least one additional month to increase the concentration of nanoparticles in the mixture. The mixture was then filtered a second time in Whatman qualitative filter paper grade 1. The filtrate was next filtered in a vacuum chamber, with a 47 mm diameter glass microfiber filter, pore size of 1.1 μm.

To determine the purity of the extract, 10μl of the extract was mixed with 5 μl of acridine orange and placed on a glass microscope slide. The mixture was examined on an immunofluorescence optical microscope at 400× magnification. The extract quality was considered optimum when only fast moving small nanoparticles (30-150 nm) were visible. If large brilliant red particles (0.15-0.24 um) were observed in the mixture at a concentration of ≧1.0 large particle/visual field, the extract was submitted to tangential flow filtration in the Minitan Ultrafiltration System (Millipore, Bedford, Mass., USA), using the microporous membrane packet (30,000 NMWL) that concentrates large particles. The filtrate was then used in the experiments.

Production of Orchid Gel

The purified orchid extract was diluted 1:5 in thermal water (from Irai-RS, Brazil), which was previously boiled and filtered. The diluted orchid extract was then mixed in an anionic gel (Dermavita, Brusque, Santa Catarina, Brazil) until the mixture achieved a final concentration of 15% orchid extract.

Production of Trans-Sialidase

Purified trans-sialidase was produced from the *Escherichia coli* BLB21 DE3 inserted with the pTSII plasmidium, as described previously (International Patent application no. PCT/BR01/00083, filed Jul. 3, 2001).

Production of Trans-Sialidase Gel

Pure recombinant trans-sialidase was diluted 1:250,000 in MilliQ purified water. The diluted trans-sialidase was then mixed into Natrosol® gel (Dermavita, Brusque, Santa Catarina, Brazil), at a concentration of 1:1 and stored at 4° C. The trans-sialidase enzymatic activity of the gel mixture was between 2,000-5,000 CPM.

Production of a Trans-Sialidase-Orchid Gel Mixture.

A combined mixture of the orchid extract gel and trans-sialidase gel was created by mixing the two together. The two gels were combined to produce a final gel mixture that was 20% orchid extract gel and 80% trans-sialidase gel, or was in an orchid extract gel:trans-sialidase gel ration of 1:1, 1:2.5, 1:6 or 1:20.

Treatment with Orchid Extract Gel and Trans-Sialidase Gel

Thirty one patients presenting severe skin lesions including edema and redness, in the most severe cases associated with ulcers, caused by radiodermatitis after radiotherapy (median 5040 cGy; radiodermatitis degree 2-4) were treated with orchid extract gel and trans-sialidase gel. Treatment with the gels was administered between intervals of radiotherapy. Patients received treatment with the gels for a one year period. 26 patients were receiving radiotherapy for malignant neoplasia, and 5 patients were receiving radiotherapy for different inflammatory cutaneous discontinuities (Table II). Patients were treated with daily topical application (1.0 ml /50 cm2 of cutaneous surface) of trans-sialidase gel (once in the morning) and orchid gel (once in the evening). An additional 7 patients presenting radiodermatitis grade 3-4 lesions received treatment with a combined orchid extract gel and trans-sialidase gel during the treatment period.

Results

The 7 patients treated with the combined mixture of orchid extract gel and trans-sialidase gel, and 30 of the 31 patients treated with the once daily applications of the trans-sialidase gel and the orchid extract gel separately exhibited a decrease of edema and redness within two to eight days of treatment, along with healing of ulcers (FIG. 1). Untreated lesions require between at least 20-30 days for healing to occur. One patient who was receiving chemotherapy in combination with radiotherapy during the study did not exhibit a decrease in edema or redness.

TABLE II

Clinical data of the 31 patients treated with trans-sialidase gel and orchid extract gel.

| Case | Sex/age | Diagnosis | Radiodermatitis degree |
|---|---|---|---|
| 1. | F/50 y | Breast cancer | 2 |
| 2. | F/42 | Breast cancer | 2 |
| 3. | F/54 | Breast cancer | 2 |
| 4. | F/63 | Breast cancer | 3 |
| 5. | F/69 | Breast cancer | 3 |
| 6. | F/62 | Breast cancer | 2 |
| 7. | M/32 | Melanoma | 2 |
| 8. | F/58 | Breast cancer | 2 |
| 9. | M/54 | Larynx cancer | 3 |
| 10. | F/38 | Melanoma | 4 |
| 11. | F/62 | Breast cancer | 3 |
| 12. | F/45 | Breast cancer | 3 |
| 13. | M/67 | Rectum cancer | 4 |
| 14. | F/64 | Breast cancer | 2 |
| 15. | F/38 | Breast cancer | 3 |
| 16. | F/49 | Breast cancer | 2 |
| 17. | F/28 | skin dehiscence | — |
| 18. | F/28 | Breast cancer | 3 |
| 19. | F/46 | Breast cancer | 4 |
| 20. | F/63 | Breast cancer | 2 |
| 21. | F/50 | Breast cancer | 3 |
| 22. | F/70 | Breast cancer | 2 |
| 23. | F/84 | Breast cancer | 2 |
| 24. | F/58 | Breast cancer | 2 |
| 25. | F/57 | Thymoma | 3 |
| 26. | F/50 | Breast cancer | 2 |
| 27. | F/62 | foreign body reaction | — |
| 28. | M/62 | fistulae | — |
| 29. | M/61 | skin dehiscence | — |
| 30. | F/51 | Legs chronic dermatitis | — |
| 31. | M/71 | Chemotherapy ulcers | — |

Example 2

Figure 2:
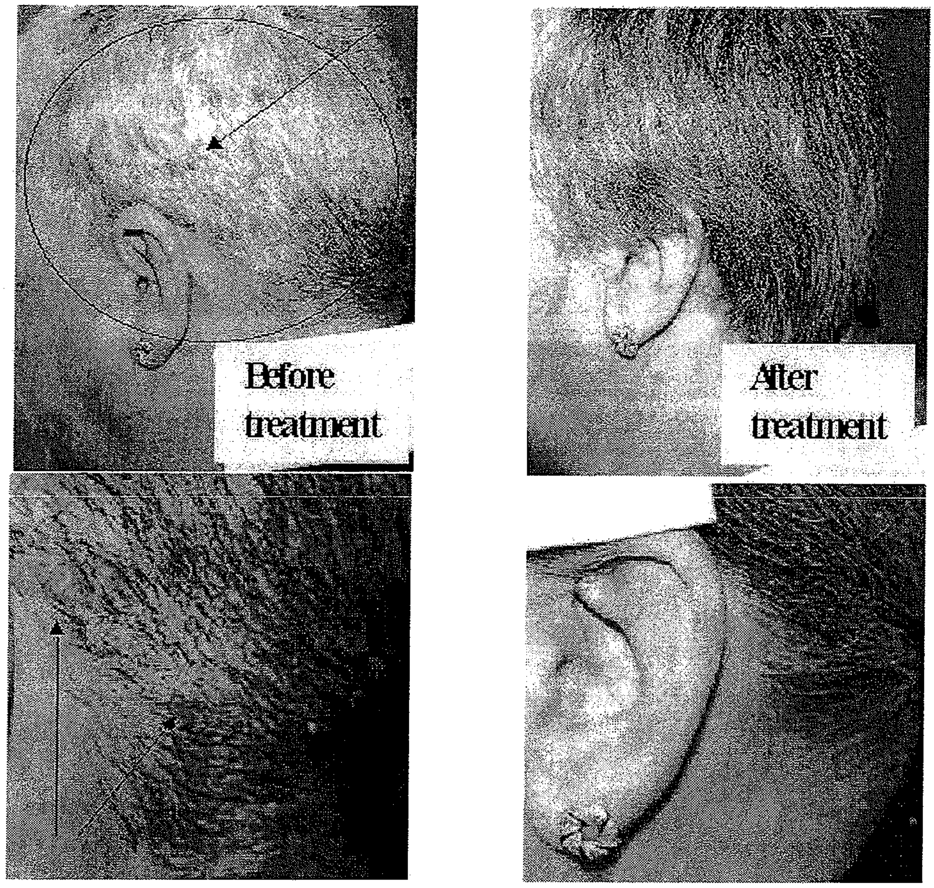

Treatment of Psoriasis and Psoriatic Arthritis with Trans-Sialidase Gel and Orchid Extract Gel A 59 years old woman with severe psoriasis of the scalp, as well as many other parts of the body, was treated with the trans-sialidase and orchid extract gels. The two gels were prepared as described previously. The patient was treated by topical application of the gels once per day for two months. The trans-sialidase gel was applied in the morning, and the orchid extract gel was applied at night during each day of treatment. Following treatment, the psoriasis of the scalp regressed, exhibiting a decrease in the presence of the skin lesions (FIG. 2).

A 47 year old woman with severe psoriatic arthritis received treatment with the trans-sialidase and orchid extract gels, prepared as previously described. The psoriatic arthritis presented as inflammation of the joints associated with psoriasis of the scalp, arms, hands, and legs. The psoriatic arthritis was characterized by retraction and immobilization of the fingers, and difficulty in raising the arms. Immunohistochemical analysis performed on cutaneous biopsies as previously described in Higuchi et al., 2006, APMIS 114:338-344, revealed a high presence of *Mycoplasma pneumoniae* and *Chlamydia pneumoniae* antigens on the affected tissue. The patient was treated for one year with both trans-sialidase and orchid extract gels. Each gel was applied once per day with the trans-sialidase gel applied in the morning, and the orchid extract gel applied at night. Following one year of treatment, the patient experienced a decrease in the presence of skin lesions, and an increase in mobility of the fingers and arms.

Example 3

Treatment of Joint and Column Pain with Trans-Sialidase Gel and Orchid Extract Gel Ten patients suffering from joint and column pain, which was associated with articulation inhibition, were treated with the orchid extract gel or a mixture of both the orchid extract gel and the trans-sialidase gel for more than one year.

Three patients that were at least 65 years of age topically applied the orchid extract gel each time joint or column pain was experienced. Treated patients reported pain relief to be immediate, or within one hour after treatment with the orchid gel, and the relief lasted at least one day.

Seven patients aged 35 to 65 years with articular and muscle pain due to arthritis of different etiologies, bursitis and idiopathic myalgia, were treated with a combined orchid extract gel and trans-sialidase gel mixed at a ration of 1:1. The combined gel was applied twice a day (once every twelve hours) during a 15-30 day treatment period. Pain relief occurred in less than one hour following treatment and persisted during the entire treatment period.

Various publications are cited herein, the contents of which are hereby incorporated by reference in their entireties.

What is claimed is:

1. A method of promoting healing of a lesion by applying a composition comprising an agent capable of removing sialic acid residues at the site of the lesion and one or more plant extracts comprising nucleic acid-containing particles selected from the group consisting of archaea, nanoarchaea, and a mixture thereof.

2. The method of claim 1, wherein the composition is applied topically to the lesion.

3. The method of claim 1, wherein the lesion is selected from the group consisting of a cutaneous, a mucosal and a mucocutaneous lesion.

4. The method of claim 1, wherein the agent that can remove sialic acid residues is an enzyme selected from the group consisting of a trans-sialidase, neuraminidase, and a combination of a trans-sialidase and a neuraminidase.

5. The method of claim 1, wherein the plant extract is an extract from a plant selected from the group consisting of garlic, ginkgo, tomato, orchid, guava, ginseng, ginger, and tobacco.

6. The method of claim 1, wherein the agent further comprises a metal chelator.

7. The method of claim 6, wherein the metal chelator is pyrrolidine dithiocarbamate (PDTC).

* * * * *

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 1

ggaattccat atggcacccg gatcgagc                                          28


<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 2

cggatccggg cgtacttctt tcactggtgc cggt                                   34


<210> SEQ ID NO 3
<211> LENGTH: 2010
<212> TYPE: DNA
<213> ORGANISM: Artificial Sequence
<220> FEATURE:
<223> OTHER INFORMATION: Variant of T. Cruzi trans-sialidase gene.

<400> SEQUENCE: 3

atgggcagca gccatcatca tcatcatcac agcagcggcc tggtgccgcg cggcagccat      60

atggcacccg gatcgagccg agttgagctg tttaagcggc aaagctcgaa ggtgccattt     120

gaaaagggcg gcaaagtcac cgagcgggtt gtccactcgt tccgcctccc cgcccttgtt     180

aatgtggacg gggtgatggt tgccatcgcg gacgctcgct acgaaacatc caatgacaac     240

tccctcattg atacggtggc gaagtacagc gtggacgatg gggagacgtg ggagacccaa     300

attgccatca agaacagtcg tgcatcgtct gtttctcgtg tggtggatcc cacagtgatt     360

gtgaagggca acaagcttta cgtcctggtt ggaagctaca acagttcgag gagctactgg     420

acgtcgcatg gtgatgcgag agactgggat attctgcttg ccgttggtga ggtcacgaag     480

tccactgcgg gcggcaagat aactgcgagt atcaaatggg ggagccccgt gtcactgaag     540

gaatttttcc cggcggaaat ggaaggaatg cacacaaatc aatttcttgg cggtgcaggt     600

gttgccattg tggcgtccaa cgggaatctt gtgtaccctg tgcaggttac gaacaaaaag     660
```

-continued

```
aagcaagttt tttccaagat cttctactcg gaagacgagg gcaagacgtg gaagtttggg    720

gagggtagga gtgattttgg ctgctctgaa cctgtggccc ttgagtggga ggggaagctc    780

atcataaaca ctcgagttga ctatcgccgc cgtctggtgt acgagtccag tgacatgggg    840

aattcgtggg tggaggctgt cggcacgctc tcacgtgtgt ggggcccctc accaaaatcg    900

aaccagcccg gcagtcagag cagcttcact gccgtgacca tcgagggaat gcgtgttatg    960

ctcttcacac acccgctgaa ttttaaggga aggtggctgc gcgaccgact gaacctctgg   1020

ctgacggata accagcgcat ttataacgtt gggcaagtat ccattggtga tgaaaattcc   1080

gcctacagct ccgtcctgta caaggatgat aagctgtact gtttgcatga gatcaacagt   1140

aacgaggtgt acagccttgt tttgcgcgc ctggttggcg agctacggat cattaaatca    1200

gtgctgcagt cctggaagaa ttgggacagc cacctgtcca gcatttgcac ccctgctgat   1260

ccagccgctt cgtcgtcaga gcgtggttgt ggtcccgctg tcaccacggt tggtcttgtt   1320

ggctttttgt cgcacagtgc caccaaaacc gaatgggagg atgcgtaccg ctgcgtcaac   1380

gcaagcacgg caaatgcgga gagggttccg aacggtttga agtttgcggg ggttggcgga   1440

ggggcgcttt ggccggtgag ccagcagggg cagaatcaac ggtatcactt tgcaaaccac   1500

gcgttcacgc tggtggcgtc ggtgacgatt cacgaggttc cgagcgtcgc gagtcctttg   1560

ctgggtgcga gcctggactc ttctggtggc aaaaaactcc tggggctctc gtacgacgag   1620

aagcaccagt ggcagccaat atacggatca acgccggtga cgccgaccgg atcgtgggag   1680

atgggtaaga ggtaccacgt ggttcttacg atggcgaata aaattggttc ggtgtacatt   1740

gatggagaac ctctggaggg ttcagggcag accgttgtgc cagacgggag gacgcctgac   1800

atctcccact tctacgttgg cgggtatgga aggagtgata tgccaaccat aagccacgtg   1860

acggtgaata atgttcttct ttacaaccgt cagctgaatg ccgaggagat caggaccttg   1920

ttcttgagcc aggacctgat tggcacggaa gcacacatgg gcagcagcag cggcagcagt   1980

gaaagaagta cgcccggatc cggctgctaa                                    2010
```

```
<210> SEQ ID NO 4
<211> LENGTH: 669
<212> TYPE: PRT
<213> ORGANISM: Artificial Sequence
<220> FEATURE:
<223> OTHER INFORMATION: Variant of T. Cruzi trans-sialidase protein.

<400> SEQUENCE: 4

Met Gly Ser Ser His His His His His His Ser Ser Gly Leu Val Pro
1               5                   10                  15

Arg Gly Ser His Met Ala Pro Gly Ser Ser Arg Val Glu Leu Phe Lys
            20                  25                  30

Arg Gln Ser Ser Lys Val Pro Phe Glu Lys Gly Gly Lys Val Thr Glu
        35                  40                  45

Arg Val Val His Ser Phe Arg Leu Pro Ala Leu Val Asn Val Asp Gly
    50                  55                  60

Val Met Val Ala Ile Ala Asp Ala Arg Tyr Glu Thr Ser Asn Asp Asn
65                  70                  75                  80

Ser Leu Ile Asp Thr Val Ala Lys Tyr Ser Val Asp Asp Gly Glu Thr
                85                  90                  95

Trp Glu Thr Gln Ile Ala Ile Lys Asn Ser Arg Ala Ser Ser Val Ser
            100                 105                 110

Arg Val Val Asp Pro Thr Val Ile Val Lys Gly Asn Lys Leu Tyr Val
        115                 120                 125
```

-continued

```
Leu Val Gly Ser Tyr Asn Ser Ser Arg Ser Tyr Trp Thr Ser His Gly
    130                 135                 140

Asp Ala Arg Asp Trp Asp Ile Leu Leu Ala Val Gly Glu Val Thr Lys
145                 150                 155                 160

Ser Thr Ala Gly Gly Lys Ile Thr Ala Ser Ile Lys Trp Gly Ser Pro
                165                 170                 175

Val Ser Leu Lys Glu Phe Phe Pro Ala Glu Met Glu Gly Met His Thr
            180                 185                 190

Asn Gln Phe Leu Gly Gly Ala Gly Val Ala Ile Val Ala Ser Asn Gly
        195                 200                 205

Asn Leu Val Tyr Pro Val Gln Val Thr Asn Lys Lys Lys Gln Val Phe
    210                 215                 220

Ser Lys Ile Phe Tyr Ser Glu Asp Glu Gly Lys Thr Trp Lys Phe Gly
225                 230                 235                 240

Glu Gly Arg Ser Asp Phe Gly Cys Ser Glu Pro Val Ala Leu Glu Trp
                245                 250                 255

Glu Gly Lys Leu Ile Ile Asn Thr Arg Val Asp Tyr Arg Arg Arg Leu
            260                 265                 270

Val Tyr Glu Ser Ser Asp Met Gly Asn Ser Trp Val Glu Ala Val Gly
        275                 280                 285

Thr Leu Ser Arg Val Trp Gly Pro Ser Pro Lys Ser Asn Gln Pro Gly
    290                 295                 300

Ser Gln Ser Ser Phe Thr Ala Val Thr Ile Glu Gly Met Arg Val Met
305                 310                 315                 320

Leu Phe Thr His Pro Leu Asn Phe Lys Gly Arg Trp Leu Arg Asp Arg
                325                 330                 335

Leu Asn Leu Trp Leu Thr Asp Asn Gln Arg Ile Tyr Asn Val Gly Gln
            340                 345                 350

Val Ser Ile Gly Asp Glu Asn Ser Ala Tyr Ser Ser Val Leu Tyr Lys
        355                 360                 365

Asp Asp Lys Leu Tyr Cys Leu His Glu Ile Asn Ser Asn Glu Val Tyr
    370                 375                 380

Ser Leu Val Phe Ala Arg Leu Val Gly Glu Leu Arg Ile Ile Lys Ser
385                 390                 395                 400

Val Leu Gln Ser Trp Lys Asn Trp Asp Ser His Leu Ser Ser Ile Cys
                405                 410                 415

Thr Pro Ala Asp Pro Ala Ala Ser Ser Ser Glu Arg Gly Cys Gly Pro
            420                 425                 430

Ala Val Thr Thr Val Gly Leu Val Gly Phe Leu Ser His Ser Ala Thr
        435                 440                 445

Lys Thr Glu Trp Glu Asp Ala Tyr Arg Cys Val Asn Ala Ser Thr Ala
    450                 455                 460

Asn Ala Glu Arg Val Pro Asn Gly Leu Lys Phe Ala Gly Val Gly Gly
465                 470                 475                 480

Gly Ala Leu Trp Pro Val Ser Gln Gln Gly Gln Asn Gln Arg Tyr His
                485                 490                 495

Phe Ala Asn His Ala Phe Thr Leu Val Ala Ser Val Thr Ile His Glu
            500                 505                 510

Val Pro Ser Val Ala Ser Pro Leu Leu Gly Ala Ser Leu Asp Ser Ser
        515                 520                 525

Gly Gly Lys Lys Leu Leu Gly Leu Ser Tyr Asp Glu Lys His Gln Trp
    530                 535                 540
```

-continued

```
Gln Pro Ile Tyr Gly Ser Thr Pro Val Thr Pro Thr Gly Ser Trp Glu
545                 550                 555                 560

Met Gly Lys Arg Tyr His Val Val Leu Thr Met Ala Asn Lys Ile Gly
                565                 570                 575

Ser Val Tyr Ile Asp Gly Glu Pro Leu Glu Gly Ser Gly Gln Thr Val
            580                 585                 590

Val Pro Asp Gly Arg Thr Pro Asp Ile Ser His Phe Tyr Val Gly Gly
        595                 600                 605

Tyr Gly Arg Ser Asp Met Pro Thr Ile Ser His Val Thr Val Asn Asn
    610                 615                 620

Val Leu Leu Tyr Asn Arg Gln Leu Asn Ala Glu Glu Ile Arg Thr Leu
625                 630                 635                 640

Phe Leu Ser Gln Asp Leu Ile Gly Thr Glu Ala His Met Gly Ser Ser
                645                 650                 655

Ser Gly Ser Ser Glu Arg Ser Thr Pro Gly Ser Gly Cys
            660                 665
```